United States Patent
Hegstad et al.

(10) Patent No.: US 8,431,775 B2
(45) Date of Patent: Apr. 30, 2013

(54) METHODS AND COMPOSITIONS FOR ENHANCED YIELD BY TARGETED EXPRESSION OF KNOTTED1

(75) Inventors: Jeffrey M. Hegstad, Ankeny, IA (US); Jeffrey E. Habben, Urbandale, IA (US); Nicholas J. Bate, Urbandale, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 196 days.

(21) Appl. No.: 12/631,349

(22) Filed: Dec. 4, 2009

(65) Prior Publication Data

US 2011/0078822 A1    Mar. 31, 2011

Related U.S. Application Data

(60) Provisional application No. 61/119,918, filed on Dec. 4, 2008.

(51) Int. Cl.
*A01H 5/00* (2006.01)
*A01H 5/10* (2006.01)
*C12N 15/82* (2006.01)

(52) U.S. Cl.
USPC ........ 800/298; 800/320.1; 800/278; 800/287; 800/290

(58) Field of Classification Search .................. None
See application file for complete search history.

(56) References Cited

U.S. PATENT DOCUMENTS

2003/0233670 A1    12/2003    Edgerton

OTHER PUBLICATIONS

Williams-Carrier et al (1997, Development 124:3737-3745).*
Postma-Haarsma et al (1999, Plant Molecular Biology 39:257-271).*
Matsuoka, M., et al.; "Expression of a Rice Homeobox Gene Causes Altered Morphology of Transgenic Plants"; The Plant Cell (Sep. 1993) 5:1039-1048; American Society of Plant Physiologists; Rockville, MD.
Ori, N., et al.; "Leaf Senescence is Delayed in Tobacco Plants Expressing the Maize Homeobox Gene knotted1 under the Control of a Senescence-Activated Promoter"; The Plant Cell (Jun. 1999) 11:1073-1080; American Society of Plant Physiologists; Rockville, MD.
Vollbrecht, E., et al.; "The developmental gene Knotted-1 is a member of a maize homeobox gene family"; Nature (Mar. 21, 1991) 350:241-243; Nature Publishing Group; London, UK.
Kerstetter, R., et al.; "Loss-of-function mutations in the maize homeobox gene, knotted1, are defective in shoot meristem maintenance"; Development (1997) 124:3045-3054; The Company of Biologists Limited, Great Britain.
Smith, L., et al.; "A dominant mutation in the maize homeobox gene, Knotted-1, causes its ectopic expression in leaf cells with altered fates"; Development (1992) 116:21-30; The Company of Biologists Limited, Great Britain.
Sakamoto, T., et al.; "Ectopic Expression of KNOTTED1-Like Homeobox Protein Induces Expression of Cytokinin Biosynthesis Genes in Rice"; Plant Physiology (Sep. 2006) 142:54-62; American Society of Plant Biologists; Rockville, MD.
Hay, A. and Tsiantis, M.; "A Knox family Tale"; Current Opinion in Plant Biology (2009) 12:593-598; Elsevier, Inc.; Amsterdam, The Netherlands.
Genbank Accession No. AY260164.1; "*Zea mays* KNOTTED1 (kn1) gene, complete cds", 2003.

* cited by examiner

*Primary Examiner* — Stuart F Baum
(74) *Attorney, Agent, or Firm* — Pioneer Hi-Bred Int'l Inc.

(57) ABSTRACT

Methods and compositions for modulating expression of knotted1 (kn1) polypeptides in seed and reproductive tissue are provided. Polynucleotide sequences encoding knotted1 transcription factor polypeptides are expressed in a spatially and/or temporally regulated manner with expression preferentially in developing flowers, pods, ears and/or seeds, or to other reproductive structures during flowering and seed development, to create a sequestered effect resulting in plants that produce increased yield and may have greater flower, pod, ear and/or seed retention. Transformed plants, plant cells, tissues and seed are also provided.

18 Claims, 10 Drawing Sheets

General Description
DNA PHP24677A
GM-SAMS PRO:GM-HRA:GM-ALS (HRA) TERM+GM-ANN PRO+ZM-KN1:PINII TERM.
length: 7555 bp
storage type: Basic
form: Linear Functional Map CDS (2 signals)

ZM-KNOTTED1
     Start: 378   End: 1457  (Complementary)

GM-HRA
     Start: 4886  End: 6853
     soybean ALS gene with HrA mutations pro ->ala, tr Intron (1 signal)

GM-SAMS INTRON1
     Start: 4279  End: 4869
     INTRON1 of GM-SAMS PRO (part of original GM-SAMS PRO feature.

Promoter_prokaryotic (2 signals)

GM-ANN PRO
     Start: 1467  End: 3484  (Complementary)
     SOYBEAN ANNEXIN PRO GM-SAMS PRO
     Start: 3576  End: 4219
     soy SAMS 1.3 kb promoter Terminator (2 signals)

PINII TERM
     Start: 29    End: 347   (Complementary)
     Potato PINII terminator GM-ALS (HRA) TERM
     Start: 6857  End: 7508
        (MERGE: GM-ALS (HRA) TERM)

5'UTR (2 signals)

GM-SAMS 5UTR
     Start: 4220  End: 4278
     5' UTR of GM-SAMS PRO (part of original GM-SAMS PRO feature.

GM-SAMS 5UTR (2)
     Start: 4870  End: 4885
     SECOND 5' UTR region of GM-SAMS PRO (part of original GM-SAMS PRO feature.

Restriction Map

ApaLI: 1 site   GTGCAC
                  CACGTG
     N1: 1637

AvaI: 3 sites   CYCGRG
                  GRGCYC
     N1: 23
     N2: 1090
     N3: 7545

FIG. 2A

Attorney Docket Number: 2831+

BamHI: 3 sites  G|GATCC
                CCTAG|G
   N1: 1459
   N2: 4385
   N3: 6807

ClaI: 0 sites  AT|CGAT
               TAGC|TA

EcoRI: 3 sites  G|AATTC
                CTTAA|G
   N1: 1514
   N2: 4682
   N3: 5777

HindIII: 5 sites  A|AGCTT
                  TTCGA|A
   N1: 3174
   N2: 3188
   N3: 3278
   N4: 3567
   N5: 5985

NcoI: 4 sites  C|CATGG
               GGTAC|C
   N1: 1406
   N2: 1455
   N3: 1463
   N4: 6379

PstI: 2 sites  CTGCA|G
               G|ACGTC
   N1: 905
   N2: 1241

SmaI: 1 site  CCC|GGG
              GGG|CCC
   N1: 7547

Annotations

FIG. 2B

```
                                                    M  D  P  W
                        AAAGTT AACTAAGAAG CAATACTTCC ATGGATCCAT

E  E  I  T  Q  H  F  G  V  G  A  S  S  H  G  H  G  Q  H  G  Q  H  H  H  H  H  H  H  P  W  A  S
GGAGAGATC ACCCAACACT TTGGAGTTGG CGCAAGCAGC CACGGCCATG CAAGCAGCCA GCACCACCAC CATCACCACC ACCACCACCC GTGGGCATCC

S  L  S  A  V  V  A  P  L  P  P  Q  P  P  S  A  G  L  P  L  T  L  N  T  V  A  A  T  G  N  S  G  G  S
TCCCTCAGCG CCGTCGTAGC CGCTGCCG CCGCAACCGC CAAGCGCAGG CCTGCCGCTG ACCCTGAACA CGGTGGCGGC CACTGGGAAC AGCGGCGGTA
```

FIGURE 3

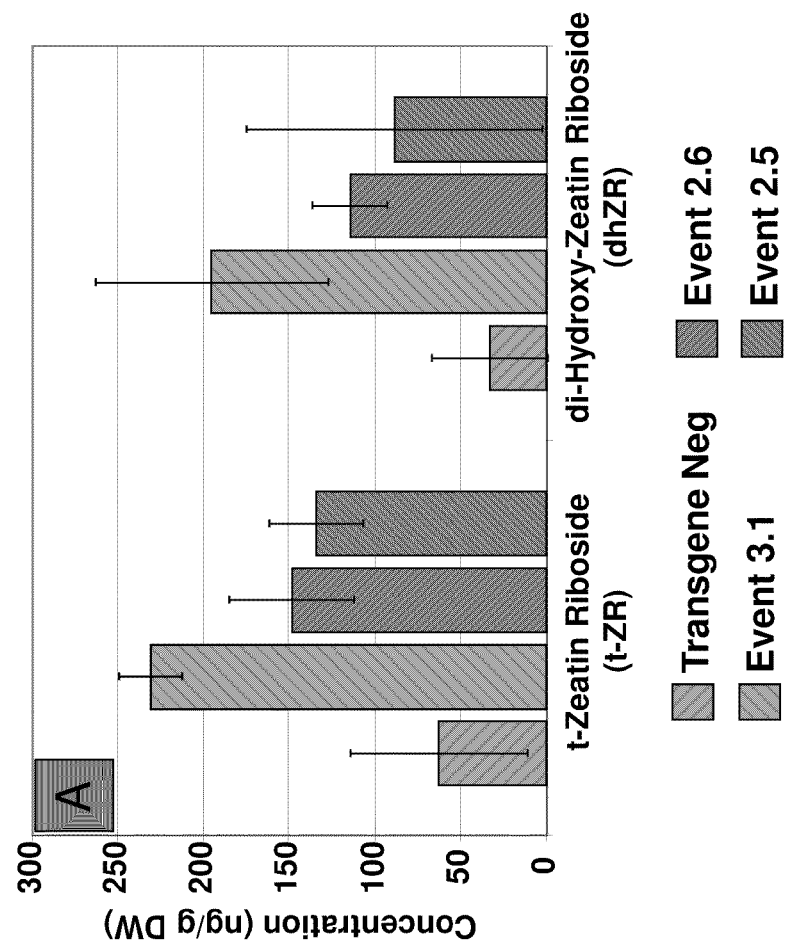
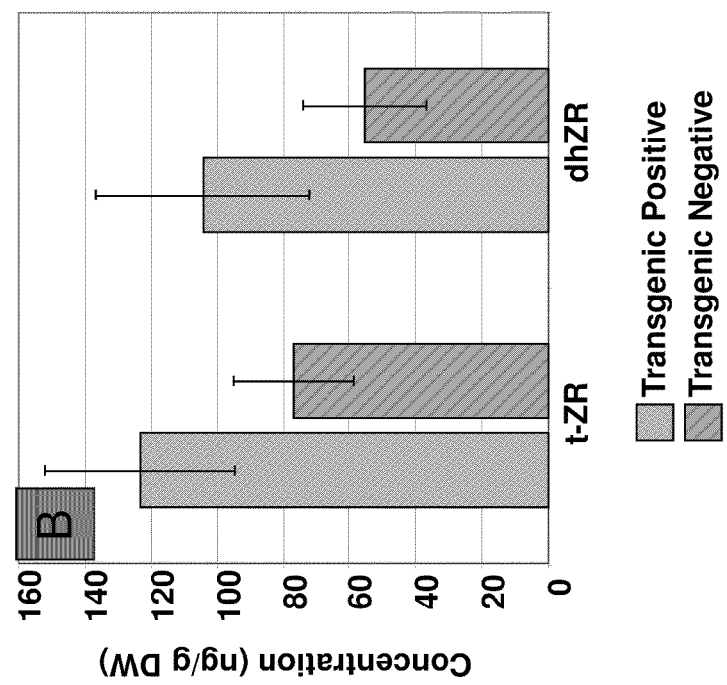
FIG. 5

PHP35999A

General Description

Standard Fields

Author

Original Author

Comments

Annotations

Feature Map

CDS (2 total)

ZM-KNOTTED1

Start: 515 End: 1594 (Complementary)
            Original Location Description:
                complement(515..1594)

GM-ALS

Start: 4992 End: 6962
            Original Location Description:
                4992..6962

Intron (1 total)

GM-SAMS INTRON1

Start: 4385 End: 4975
            INTRON1 of GM-SAMS PRO (part of original GM-SAMS PRO feature.
            Original Location Description:
                4385..4975

Misc. Feature (2 total)

ATTB2

Start: 57 End: 77
            Original Location Description:
                57..77

ATTB1

Start: 3692 End: 3712 (Complementary)
            Original Location Description:
                complement(3692..3712)

Promoter Eukaryotic (2 total)

GM-ANN PRO

Start: 1601 End: 3618 (Complementary)
            Original Location Description:
                complement(1601..3618)

GM-SAMS PRO

FIG. 8A

Start: 3716 End: 4325
soy SAMS 1.3 kb promoter
Original Location Description:
3716..4325

Terminator (2 total)

PINII TERM

Start: 151 End: 468 (Complementary)
Potato PINII terminator
Original Location Description:
complement(151..468)

GM-ALS (HRA) TERM

Start: 6963 End: 7617
(MERGE: GM-ALS (HRA) TERM)
Original Location Description:
6963..7617

5' UTR (2 total)

GM-SAMS 5UTR

Start: 4326 End: 4384
5' UTR of GM-SAMS PRO (part of original GM-SAMS PRO feature.
Original Location Description:
4326..4384

GM-SAMS 5UTR (2)

Start: 4976 End: 4991
SECOND 5' UTR region of GM-SAMS PRO (part of original GM-SAMS PRO feature.
Original Location Description:
4976..4991

Restriction/Methylation Map

ApaLI: 1 site

AvaI: 4 sites

BamHI: 3 sites

ClaI: 0 sites

EcoRI: 5 sites

HindIII: 5 sites

NcoI: 3 sites

PstI: 2 sites

SmaI: 2 sites

XmaI: 2 sites

FIG. 8B

SEQUENCE LISTING

```
<160> NUMBER OF SEQ ID NOS: 7

<210> SEQ ID NO 1
<211> LENGTH: 7555
<212> TYPE: DNA
<213> ORGANISM: Artificial Sequence
<220> FEATURE:
<223> OTHER INFORMATION: Zea mays; Glycine max; synthesized

<400> SEQUENCE: 1
cgcgccggta ccgggccccc cctcgagcgg ccgcaattcg caaaacacac ctagactaga     60
tttgttttgc taacccaatt gatattaatt atatatgatt aatatttata tgtatatgga    120
```

```
tttggttaat gaaatgcatc tggttcatca aagaattata aagcacgtg acattcattt      180 aggataagaa atatggatga tctctttctc ttttattcag ataactagta attacacata     240
acacacaact tgatgccca cattatagtg attagcatgt cactatgtgt gcatccttt       300 atttcataca ttaattaagt tggccaatcc agaagatgga caagtctagg ttaacaatgg    360
aagcgagata ccggtggcta gccgagccgg tacagcccgc cgtcgttgat gaagtggccg   420
tccatgtaga aggcattggt ggtgtggtac ccgtccatca tcaggtggtg catctcctcg   480
gatggcttcc agtgccgctt ccgctggttg atgaaccagt tgttgatctg cttcaggtca   540
agcccggtag actcagccag tgccaccttc tgagtctctg aggggtaagg ccatttgtag   600
tgctgatccc accagctaag gagctgctgg cgagcctcct tggggagctt ccctttcttc   660
ttcttctttg acagttcttg cttgagcgag cttagatagc cactgtattt cttcaggaga   720
tggtgcttca gctcttggtc cacaccatgt gcatcaactt cagggagctc ggtctctcct   780
ccgctacctt cttgatcctc ctcagaagag ccagatgaaa ggatgttgcg cagcgacctt   840
ccggagatgg aaagcgagtt cagctgcgac tccacccttc gcatgaactc catcgcctcc   900
tgcagcggcc tcgtcagctc ctccctgaac ttcaccagca tctcgtggta cgcctccatg   960
aactggtcca gctccggctc cgtcgcagcg gccaggccgc cgagcgccgt gcgctgccgc  1020
gcctccacct cctgcgctat ctccgtcagc ctcgccgaca cctccggtgg tgccccacc   1080 ttgttgcact cgaggtaggc agtgaggagc gagtagtagt gtgggtgcga gatgatcttg  1140
gccttgatgg cctcgacgtc gcctgcgtag ggagacgacg acgagggctc cttcgccttg  1200
acgcatgcgt cgaggaggcc gccaccgttg gcaagctgca gcaccgggtt gccgctaccg  1260
ccgctgttcc cagtggccgc caccgtgttc agggtcagcg gcaggcctgc gcttggcggt  1320
tgcggcggca gcggcgctac gacggcgctg agggaggatg cccacgggtg gtggtggtgg  1380
tgatgatggt ggtgctggcc gtggccatgg ccgtggctgc ttgcgccaac tccaaagtgt  1440
tgggtgatct cctccatgga tccatggaag tattgcttct tagttaacct ttcctttctc  1500
tctcagctat gtgaattcat tttgctttcg tcacaattta tatagtgaaa ttggatcttt   1560
ggagttaacg ccttcacagg attatcgtgt tagaacaatg cttttttcatg ttctaattag  1620 tagtacatta caaatgtgca ctctattcaa taagcatctt ttggcacgtt aataaatcat   1680
gtgaaaaaaa aatactacta tttcaaagaa agtgttgtaa aaagaaacgg aaagagagct  1740
ggcttcagtt gttgagactt gtttgctagt aaaaatggtg tgaagagtga ttcatggtga  1800
ggtggttttt cgtcccttc tgtttgcatg aaaaacaaat ggcaagagat gacgtaggat    1860
tccttccctt aacgattatc tgtttttaat ttcaaatata catataggaa tttatgaatt   1920
actaaggttg taaatatgc tggtcattta tttatggcta aaatatttt ttttctcgta     1980 aatataaaaa tatttaaaat ttatttttat catattttt atccttataa aattatgtgt    2040
acaacctata taaaaaata tcatatttaa tattgattat atgtttaatc aatataaaaa   2100
atcattatca tatatttaga tttattcgaa tatacatcta aacaaaaaat aacatatttt   2160
aattttatga agaaaaaaa atattttatc ctttatttat ttaagattaa ttaatagtta    2220
tgtattgtgg aaagactttt acacatgcaa tagatatact gaatcaatta gatgccaatg  2280
ctgagttgga aatcacttga ggaggggagg agacttgcca atgctttca gtttcattta   2340 aatgatttag tggaggagat agagtagtga taaaggcatg ccccaatttt ggagtgtata  2400
tatgagtgga aataagagag ggatagagag aaaaaataaa gagagtaaaa ataattaatg  2460
tgaaatgata tgataaaaaa ataaagaaag agataaagag aaaaatgaaa tgagagatag  2520
```

```
atgaaataga gagtagatac atgtttgttt aggttttttt taggaaataa cacattttt    2580
tctcatcact tattactcac tgtcaatttc ctctctttca atcataatga tatgatttgt    2640
ttaacaaaaa tgtgaaaaaa catataaagt aaaatatttt tataaattga taaataaaaa    2700
tttacaaaat ttatttctta ttaaattgaa tagaaaatga aagaaagaa aagaaaagt      2760
atatataaaa tgatatagct ttaaaagaa taaattttc atatcagtct ttttttaata      2820
atttagaaat atttaagtat atagcaaaaa tataatgtac tttacatatg cataaataat    2880
aatttgaaaa tagaactaat agaatagaga aaaagtaat ataataatta actatatgaa     2940
aatttagaag ggacaatatt tttaattaag aatataaaca atatttcttt tcatgtaatg    3000
agggacggat gtacggggcc agtgttggag tcaaagccaa aatagtcacg ggaaattaa     3060
tgcactgcat gactattcga aaaaattcac tagccttact tagatgttag attaatagct    3120
aggggttgca gataattttg aaaggcatga aaacattaa tttgtacatt gcaagctttt     3180
gatgacaagc tttgcaattg ttcacactac cttatgccat ttataaatag agtgattggc    3240
atatgaagga aatcatgaga gtcgaagcga aaaacaaagc ttgagagtgt aggaaaaata    3300
cagttttttt ggtaaaaata cagtatttga ataggagcga aaaatatcct ttcaaaatga    3360
tccttttctt ttttttttt tttcttgttg ttcttggtca gttattcaaa ggaaaaggga    3420
ttgaaataaa aacttgcatg tgaatccatc taaacaccat ataatcaagg gcctaagatg    3480
gatcttctag tgatgcatat tctatagtgt cacctaaatc tgcggccgca gatttaggtg    3540
acactataga atatgcatca ctagtaagct ttgctctaga tcaaactcac atccaaacat    3600
aacatggata tcttccttac caatcatact aattattttg ggttaaatat taatcattat    3660
ttttaagata ttaattaaga aattaaaaga ttttttaaaa aatgtataaa aattatatta    3720
ttcatgattt ttcatacatt tgattttgat aataaatata tttttttta tttcttaaaa     3780
aatgttgcaa gacacttatt agacatagtc ttgttctgtt tacaaaagca ttcatcattt    3840
aatacattaa aaaatattta atactaacag tagaatcttc ttgtgagtgg tgtgggagta    3900
ggcaacctgg cattgaaacg agagaaagag agtcagaacc agaagacaaa taaaaagtat    3960
gcaacaaaca aatcaaaatc aaagggcaaa ggctggggtt ggctcaattg gttgctacat    4020
tcaattttca actcagtcaa cggttgagat tcactctgac ttccccaatc taagccgcgg    4080
atgcaaacgg ttgaatctaa cccacaatcc aatctcgtta cttaggggct tttccgtcat    4140
taactcaccc ctgccacccg gtttccctat aaattggaac tcaatgctcc cctctaaact    4200
cgtatcgctt cagagttgag accaagacac actcgttcat atatctctct gctcttctct    4260
tctcttctac ctctcaaggt acttttcttc tccctctacc aaatcctaga ttccgtggtt    4320
caatttcgga tcttgcactt ctggtttgct ttgccttgct ttttcctcaa ctgggtccat    4380
ctaggatcca tgtgaaactc tactcttctt ttaatatctg cggaatacgc gtttgacttt    4440
cagatctagt cgaaatcatt tcataattgc ctttctttct tttagcttat gagaaataaa    4500
atcacttttt ttttatttca aaataaacct tgggccttgt gctgactgag atgggggtttg   4560
gtgattacag aattttagcg aattttgtaa ttgtacttgt ttgtctgtag ttttgttttg    4620
ttttcttgtt tctcatacat tccttaggct tcaatttat tcgagtatag gtcacaatag    4680
gaattcaaac tttgagcagg ggaattaatc ccttccttca aatccagttt gtttgtatat    4740
atgtttaaaa aatgaaactt ttgctttaaa ttctattata acttttttta tggctgaaat    4800
ttttgcatgt gtcttgctc tctgttgtaa atttactgtt taggtactaa ctctaggctt     4860
gttgtgcagt ttttgaagta taaccatgcc acacaacaca atggcggcca ccgcttccag    4920
```

```
aaccacccga ttctcttctt cctcttcaca ccccaccttc cccaaacgca ttactagatc    4980 cacccctccct ctctctcatc aaaccctcac caaacccaac cacgctctca aaatcaaatg   5040
ttccatctcc aaaccccca cggcggcgcc cttcaccaag gaagcgccga ccacggagcc    5100
cttcgtgtca cggttcgcct ccggcgaacc tcgcaagggc gcggacatcc ttgtggaggc    5160
gctggagagg cagggcgtga cgacggtgtt cgcgtacccc ggcggtgcgt cgatggagat    5220
ccaccaggcg ctcacgcgct ccgccgccat ccgcaacgtg ctcccgcgcc acgagcaggg    5280
cggcgtcttc gccgccgaag gctacgcgcg ttcctccggc ctccccggcg tctgcattgc    5340
cacctccggc cccggcgcca ccaacctcgt gagcggcctc gccgacgctt taatggacag    5400
cgtcccagtc gtcgccatca ccggccaggt cgcccgccgg atgatcggca ccgacgcctt    5460
ccaagaaacc ccgatcgtgg aggtgagcag atccatcacg aagcacaact acctcatcct    5520
cgacgtcgac gacatccccc gcgtcgtcgc cgaggctttc ttcgtcgcca cctccggccg    5580
ccccggtccg gtcctcatcg acattcccaa agacgttcag cagcaactcg ccgtgcctaa    5640
ttgggacgag cccgttaacc tccccggtta cctcgccagg ctgcccaggc ccccgccga    5700 ggcccaattg gaacacattg tcagactcat catggaggcc caaaagcccg ttctctacgt    5760
cggcggtggc agtttgaatt ccagtgctga attgaggcgc tttgttgaac tcactggtat    5820
tcccgttgct agcactttaa tgggtcttgg aacttttcct attggtgatg aatattccct    5880
tcagatgctg ggtatgcatg gtactgttta tgctaactat gctgttgaca atagtgattt    5940
gttgcttgcc tttggggtaa ggtttgatga ccgtgttact gggaagcttg aggcttttgc    6000
tagtagggct aagattgttc acattgatat tgattctgcc gagattggga agaacaagca    6060
ggcgcacgtg tcggtttgcg cggatttgaa gttggccttg aagggaatta atatgatttt    6120
ggaggagaaa ggagtggagg gtaagtttga tcttggaggt tggagagaag agattaatgt    6180
gcagaaacac aagtttccat tgggttacaa gacattccag gacgcgattt ctccgcagca    6240
tgctatcgag gttcttgatg agttgactaa tggagatgct attgttagta ctggggttgg    6300
gcagcatcaa atgtgggctg cgcagtttta caagtacaag agaccgaggc agtggttgac    6360
ctcagggggt cttggagcca tgggttttgg attgcctgcg gctattggtg ctgctgttgc    6420
taaccctggg gctgttgtgg ttgacattga tggggatggt agtttcatca tgaatgttca    6480
ggagttggcc actataagag tggagaatct cccagttaag atattgttgt tgaacaatca    6540
gcatttgggt atggtggttc agttggagga taggttctac aagtccaata gagctcacac    6600
ctatcttgga gatccgtcta gcgagagcga gatattccca aacatgctca gtttgctga    6660 tgcttgtggg ataccggcag cgcgagtgac gaagaaggaa gagcttagag cggcaattca    6720
gagaatgttg gacacccctg gcccctacct tcttgatgtc attgtgcccc atcaggagca    6780
tgtgttgccg atgattccca gtaatggatc cttcaaggat gtgataactg agggtgatgg    6840
tagaacgagg tactgattgc ctagaccaaa tgttccttga tgcttgtttt gtacaatata    6900
tataagataa tgctgtccta gttgcaggat ttggcctgtg gtgagcatca tagtctgtag    6960
tagttttggt agcaagacat tttatttcc ttttatttaa cttactacat gcagtagcat    7020
ctatctatct ctgtagtctg atatctcctg ttgtctgtat tgtgccgttg gatttttttgc    7080 tgtagtgaga ctgaaaatga tgtgctagta ataatatttc tgttagaaat ctaagtagag    7140
aatctgttga agaagtcaaa agctaatgga atcaggttac atattcaatg ttttctcttt    7200
tttagcggtt ggtagacgtg tagattcaac ttctcttgga gctcacctag gcaatcagta    7260
aaatgcatat tcctttttta acttgccatt tatttactttt tagtggaaat tgtgaccaat    7320
```

| | | | |
|---|---|---|---|
| ttgttcatgt | agaacggatt | tggaccattg cgtccacaaa acgtctcttt tgctcgatct | 7380 |
| tcacaaagcg | ataccgaaat | ccagagatag ttttcaaaag tcagaaatgg caaagttata | 7440 |
| aatagtaaaa | cagaatagat | gctgtaatcg acttcaataa caagtggcat cacgtttcta | 7500 |
| gttctagacc | catcagctgg | gccggccact agtgagctcg gtacccgggt accgg | 7555 |

<210> SEQ ID NO 2
<211> LENGTH: 7626
<212> TYPE: DNA
<213> ORGANISM: Artificial Sequence
<220> FEATURE:
<223> OTHER INFORMATION: Zea mays; Glycine max; synthesized

<400> SEQUENCE: 2

| | | | |
|---|---|---|---|
| cgcgccggta | ccgggccccc | cctcgagtgc ggccgcaagc ttgtcgacgg agatcaccac | 60 |
| tttgtacaag | aaagctgggt | gcccgggaga tcggccttct aggcccggac cgggtgaccc | 120 |
| ggaccggaat | tcgagctcca | ccgcggtggc ggccgcattc gcaaaacaca cctagactag | 180 |
| atttgttttg | ctaacccaat | tgatattaat tatatatgat taatatttat atgtatatgg | 240 |
| atttggttaa | tgaaatgcat | ctggttcatc aaagaattat aaagacacgt gacattcatt | 300 |
| taggataaga | aatatggatg | atctctttct cttttattca gataactagt aattacacat | 360 |
| aacacacaac | tttgatgccc | acattatagt gattagcatg tcactatgtg tgcatccttt | 420 |
| tatttcatac | attaattaag | ttggccaatc cagaagatgg acaagtctag gttaaccatg | 480 |
| tggtacctac | gcgttcgaag | cgagataccg gtggctagcc gagccggtac agcccgccgt | 540 |
| cgttgatgaa | gtggccgtcc | atgtagaagg cattggtggt gtggtacccg tccatcatca | 600 |
| ggtggtgcat | ctcctcggat | ggcttccagt gccgcttccg ctggttgatg aaccagttgt | 660 |
| tgatctgctt | caggtcaagc | ccggtagact cagccagtgc caccttctga gtctctgagg | 720 |
| ggtaaggcca | tttgtagtgc | tgatcccacc agctaaggag ctgctggcga gcctccttgg | 780 |
| ggagcttccc | tttcttcttc | ttctttgaca gttcttgctt gagcgagctt agatagccac | 840 |
| tgtatttctt | caggagatgg | tgcttcagct cttggtccac accatgtgca tcaacttcag | 900 |
| ggagctcggt | ctctcctccg | ctaccttctt gatcctcctc agaagagcca gatgaaagga | 960 |
| tgttgcgcag | cgaccttccg | gagatggaaa gcgagttcag ctgcgactcc cccttcgca | 1020 |
| tgaactccat | cgcctcctgc | agcggcctcg tcagctcctc cctgaacttc accagcatct | 1080 |
| cgtggtacgc | ctccatgaac | tggtccagct ccggctccgt cgcagcggcc aggccgccga | 1140 |
| gcgccgtgcg | ctgccgcgcc | tccacctcct gcgctatctc cgtcagcctc gccgacacct | 1200 |
| ccggtggtgc | ccccaccttg | ttgcactcga ggtaggcagt gaggagcgag tagtagtgtg | 1260 |
| ggtgcgagat | gatcttggcc | ttgatggcct cgacgtcgcc tgcgtaggga gacgacgacg | 1320 |
| agggctcctt | cgccttgacg | catgcgtcga ggaggccgcc accgttggca agctgcagca | 1380 |
| ccgggttgcc | gctaccgccg | ctgttcccag tggccgccac cgtgttcagg tcagcggca | 1440 |
| ggcctgcgct | tggcggttgc | ggcggcagcg gcgctacgac ggcgctgagg gaggatgccc | 1500 |
| acgggtggtg | gtggtggtga | tgatggtggt gctggccgtg gccatggccg tggctgcttg | 1560 |
| cgccaactcc | aaagtgttgg | gtgatctcct ccatggatcc gaagtattgc ttcttagtta | 1620 |
| acctttcctt | tctctctcag | ctatgtgaat tcattttgct ttcgtcacaa tttatatagt | 1680 |
| gaaattggat | ctttggagtt | aacgccttca caggattatc gtgttagaac aatgcttttt | 1740 |
| catgttctaa | ttagtagtac | attacaaatg tgcactctat tcaataagca tcttttggca | 1800 |
| cgttaataaa | tcatgtgaaa | aaaaaatact actatttcaa agaaagtgtt gtaaaaagaa | 1860 |

```
acggaaagag agctggcttc agttgttgag acttgtttgc tagtaaaaat ggtgtgaaga    1920
gtgattcatg gtgaggtggt ttttcgtccc tttctgtttg catgaaaaac aaatggcaag    1980
agatgacgta ggattccttc ccttaacgat tatctgtttt taatttcaaa tatacatata    2040
ggaatttatg aattactaag gttgtaaaat atgctggtca tttatttatg ctaaaatat    2100 ttttttttct cgtaaatata aaatatttta aaatttattt ttatcatatt ttttatcctt    2160
ataaaattat gtgtacaacc tatataaaaa aatatcatat ttaatattga ttatatgttt    2220
aatcaatata aaaatcatt atcatatatt tagatttatt cgaatataca tctaaacaaa    2280
aaataacata ttttaatttt atgaagaaaa aaaaatattt tatcctttat ttatttaaga    2340
ttaattaata gttatgtatt gtggaaagac ttttacacat gcaatagata tactgaatca    2400
attagatgcc aatgctgagt tggaaatcac ttgaggaggg gaggagactt gccaatgctt    2460
ttcagtttca tttaaatgat ttagtggagg agatagagta gtgataaagg catgccccaa    2520
ttttggagtg tatatatgag tggaaataag agagggatag agagaaaaaa taagagagt     2580 aaaaataatt aatgtgaaat gatatgataa aaaaataaag aaagagataa agagaaaaat    2640
gaaatgagag atagatgaaa tagagagtag atacatgttt gtttaggttt ttttaggaa     2700 ataacacatt tttttctcat cacttattac tcactgtcaa tttcctctct ttcaatcata    2760
atgatatgat ttgtttaaca aaaatgtgaa aaaacatata aagtaaaata tttttataaa    2820
ttgataaata aaaatttaca aaatttattt cttattaaat tgaatagaaa atgaaagaaa    2880 agaaagaaa aagtatatat aaaatgatat agctttaaaa agaataaatt tttcatatca    2940
gtcttttttt aataatttag aaatatttaa gtatatagca aaaatataat gtactttaca    3000
tatgcataaa taataatttg aaaatagaac taatagaata gagaaaaaag taatataata    3060
attaactata tgaaaattta gaagggacaa tattttaat taagaatata aacaatattt     3120
cttttcatgt aatgagggac ggatgtacgg ggccagtgtt ggagtcaaag ccaaaatagt    3180
cacgggaaaa ttaatgcact gcatgactat tcgaaaaaat tcactagcct tacttagatg    3240
ttagattaat agctaggggg tgcagataat tttgaaaggc atgaaaaaca ttaatttgta    3300
cattgcaagc ttttgatgac aagctttgca attgttcaca ctaccttatg ccatttataa    3360
atagagtgat tggcatatga aggaaatcat gagagtcgaa gcgaaaaaca aagcttgaga    3420
gtgtaggaaa aatacagttt ttttggtaaa aatacagtat ttgaatagga gcgaaaaata    3480
tcctttcaaa atgatccttt tctttttttt tttttttctt gttgttcttg gtcagttatt    3540
caaaggaaaa gggattgaaa taaaaacttg catgtgaatc catctaaaca ccatataatc    3600
aagggcctaa gatggatctt ctgcggccgc caccgcggtg gagctcgaat tccggaccgg    3660
gtaacccggt ccgggccatt ctggccgag cctgcttttt tgtacaaact tgtgattctt     3720
ccttaccaat catactaatt attttgggtt aaatattaat cattattttt aagatattaa    3780
ttaagaaatt aaaagatttt ttaaaaaaat gtataaaatt atattattca tgattttca     3840 tacatttgat tttgataata aatatatttt ttttaatttc ttaaaaaatg ttgcaagaca    3900
cttattagac atagtcttgt tctgtttaca aaagcattca tcatttaata cattaaaaaa    3960
tatttaatac taacagtaga atcttcttgt gagtggtgtg ggagtaggca acctggcatt    4020
gaaacgagag aaagagagtc agaaccagaa gacaaataaa aagtatgcaa caaacaaatc    4080
aaaatcaaag ggcaaaggct ggggttggct caattggttg ctacattcaa ttttcaactc    4140
agtcaacggt tgagattcac tctgacttcc ccaatctaag ccgcggatgc aaacggttga    4200
atctaaccca caatccaatc tcgttactta ggggcttttc cgtcattaac tcaccctgc     4260
```

```
cacccggttt ccctataaat tggaactcaa tgctcccctc taaactcgta tcgcttcaga   4320
gttgagacca agacacactc gttcatatat ctctctgctc ttctcttctc ttctacctct   4380
caaggtactt ttcttctccc tctaccaaat cctagattcc gtggttcaat ttcggatctt   4440
gcacttctgg tttgctttgc cttgcttttt cctcaactgg gtccatctag gatccatgtg   4500
aaactctact ctttctttaa tatctgcgga atacgcgttt gactttcaga tctagtcgaa   4560
atcatttcat aattgccttt cttctcttta gcttatgaga aataaaatca ctttttttt   4620 atttcaaaat aaaccttggg ccttgtgctg actgagatgg ggtttggtga ttacagaatt   4680
ttagcgaatt ttgtaattgt acttgtttgt ctgtagtttt gttttgtttt cttgtttctc   4740
atacattcct taggcttcaa ttttattcga gtataggtca caataggaat caaactttg   4800 agcaggggaa ttaatcccctt ccttcaaatc cagtttgttt gtatatatgt ttaaaaaatg   4860
aaacttttgc tttaaattct attataactt tttttatggc tgaaattttt gcatgtgtct   4920
ttgctctctg ttgtaaattt actgtttagg tactaactct aggcttgttg tgcagttttt   4980
gaagtataac catgccacac aacacaatgg cggccaccgc ttccagaacc acccgattct   5040
cttcttcctc ttcacacccc accttcccca aacgcattac tagatccacc ctccctctct   5100
ctcatcaaac cctcaccaaa cccaaccacg ctctcaaaat caaatgttcc atctccaaac   5160
cccccacggc ggcgcccttc accaaggaag cgccgaccac ggagcccttc gtgtcacggt   5220
tcgcctccgg cgaacctcgc aagggcgcgg acatccttgt ggaggcgctg agaggcagg   5280 gcgtgacgac ggtgttcgcg taccccgcg gtgcgtcgat ggagatccac caggcgctca   5340
cgcgctccgc cgccatccgc aacgtgctcc cgcgccacga gcagggcggc gtcttcgccg   5400
ccgaaggcta cgcgcgttcc tccggcctcc ccggcgtctg cattgccacc tccggccccg   5460
gcgccaccaa cctcgtgagc ggcctcgccg acgctttaat ggacagcgtc ccagtcgtcg   5520
ccatcaccgg ccaggtcgcc cgccggatga tcggcaccga cgccttccaa gaaaccccga   5580
tcgtggaggt gagcagatcc atcacgaagc acaactacct catcctcgac gtcgacgaca   5640
tcccccgcgt cgtcgccgag gctttcttcg tcgccacctc cggccgcccc ggtccggtcc   5700
tcatcgacat tcccaaagac gttcagcagc aactcgccgt gcctaattgg gacgagcccg   5760
ttaacctccc cggttacctc gccaggctgc ccaggccccc cgccgaggcc caattggaac   5820
acattgtcag actcatcatg gaggcccaaa agcccgttct ctacgtcggc ggtggcagtt   5880
tgaattccag tgctgaattg aggcgctttg ttgaactcac tggtattccc gttgctagca   5940
ctttaatggg tcttggaact tttcctattg gtgatgaata ttcccttcag atgctgggta   6000
tgcatggtac tgtttatgct aactatgctg ttgacaatag tgatttgttg cttgcctttg   6060
gggtaaggtt tgatgaccgt gttactggga agcttgaggc ttttgctagt agggctaaga   6120
ttgttcacat tgatattgat tctgccgaga ttgggaagaa caagcaggcg cacgtgtcgg   6180
tttgcgcgga tttgaagttg gccttgaagg gaattaatat gattttggag gagaaaggag   6240
tggagggtaa gtttgatctt ggaggttgga gagaagagat taatgtgcag aaacacaagt   6300
ttccattggg ttacaagaca ttccaggacg cgatttctcc gcagcatgct atcgaggttc   6360
ttgatgagtt gactaatgga gatgctattg ttagtactgg ggttgggcag catcaaatgt   6420
gggctgcgca gttttacaag tacaagagac cgaggcagtg gttgacctca gggggtcttg   6480
gagccatggg ttttggattg cctgcggcta ttggtgctgc tgttgctaac cctggggctg   6540
ttgtggttga cattgatggg gatggtagtt tcatcatgaa tgttcaggag ttggccacta   6600
taagagtgga gaatctccca gttaagatat tgttgttgaa caatcagcat ttgggtatgg   6660
```

-continued

```
tggttcagtt ggaggatagg ttctacaagt ccaatagagc tcacacctat cttggagatc    6720
cgtctagcga gagcgagata ttcccaaaca tgctcaagtt tgctgatgct tgtgggatac    6780
cggcagcgcg agtgacgaag aaggaagagc ttagagcggc aattcagaga atgttggaca    6840
cccctggccc ctaccttctt gatgtcattg tgccccatca ggagcatgtg ttgccgatga    6900
ttcccagtaa tggatccttc aaggatgtga taactgaggg tgatggtaga acgaggtact    6960
gattgcctag accaaatgtt ccttgatgct tgttttgtac aatatatata agataatgct    7020
gtcctagttg caggatttgg cctgtggtga gcatcatagt ctgtagtagt tttggtagca    7080
agacatttta ttttcctttt atttaactta ctacatgcag tagcatctat ctatctctgt    7140
agtctgatat ctcctgttgt ctgtattgtg ccgttggatt ttttgctgta gtgagactga    7200
aaatgatgtg ctagtaataa tatttctgtt agaaatctaa gtagagaatc tgttgaagaa    7260
gtcaaaagct aatggaatca ggttacatat tcaatgtttt tcttttttta gcggttggta    7320
gacgtgtaga ttcaacttct cttggagctc acctaggcaa tcagtaaaat gcatattcct    7380
ttttaacttt gccatttatt tacttttagt ggaaattgtg accaatttgt tcatgtagaa    7440
cggatttgga ccattgcgtc cacaaaacgt ctcttttgct cgatcttcac aaagcgatac    7500
cgaaatccag agatagtttt caaaagtcag aaatggcaaa gttataaata gtaaaacaga    7560
atagatgctg taatcgactt caataacaag tggcatcacg tttctagttc tagacccggg    7620
taccgg                                                               7626
```

<210> SEQ ID NO 3
<211> LENGTH: 359
<212> TYPE: PRT
<213> ORGANISM: Zea mays
<220> FEATURE:
<221> NAME/KEY: MISC_FEATURE
<222> LOCATION: (137)..(147)
<223> OTHER INFORMATION: mass spectrometry tag
<220> FEATURE:
<221> NAME/KEY: MISC_FEATURE
<222> LOCATION: (298)..(309)
<223> OTHER INFORMATION: mass spectrometry tag

<400> SEQUENCE: 3

```
Met Glu Glu Ile Thr Gln His Phe Gly Val Gly Ala Ser Ser His Gly
1               5                   10                  15

His Gly His Gly Gln His His His His His His His Pro Trp
            20                  25                  30

Ala Ser Ser Leu Ser Ala Val Val Ala Pro Leu Pro Gln Pro Pro
        35                  40                  45

Ser Ala Gly Leu Pro Leu Thr Leu Asn Thr Val Ala Ala Thr Gly Asn
    50                  55                  60

Ser Gly Gly Ser Gly Asn Pro Val Leu Gln Leu Ala Asn Gly Gly Gly
65                  70                  75                  80

Leu Leu Asp Ala Cys Val Lys Ala Lys Glu Pro Ser Ser Ser Pro
                85                  90                  95

Tyr Ala Gly Asp Val Glu Ala Ile Lys Ala Lys Ile Ile Ser His Pro
            100                 105                 110

His Tyr Tyr Ser Leu Leu Thr Ala Tyr Leu Glu Cys Asn Lys Val Gly
        115                 120                 125

Ala Pro Pro Glu Val Ser Ala Arg Leu Thr Glu Ile Ala Gln Glu Val
    130                 135                 140

Glu Ala Arg Gln Arg Thr Ala Leu Gly Gly Leu Ala Ala Ala Thr Glu
145                 150                 155                 160
```

```
Pro Glu Leu Asp Gln Phe Met Glu Ala Tyr His Glu Met Leu Val Lys
                165                 170                 175
Phe Arg Glu Glu Leu Thr Arg Pro Leu Gln Ala Met Glu Phe Met
        180                 185                 190
Arg Arg Val Glu Ser Gln Leu Asn Ser Leu Ser Ile Ser Gly Arg Ser
    195                 200                 205
Leu Arg Asn Ile Leu Ser Ser Gly Ser Glu Glu Asp Gln Glu Gly
        210                 215                 220
Ser Gly Gly Glu Thr Glu Leu Pro Glu Val Asp Ala His Gly Val Asp
225                 230                 235                 240
Gln Glu Leu Lys His His Leu Leu Lys Lys Tyr Ser Gly Tyr Leu Ser
                245                 250                 255
Ser Leu Lys Gln Glu Leu Ser Lys Lys Lys Lys Gly Lys Leu Pro
        260                 265                 270
Lys Glu Ala Arg Gln Gln Leu Leu Ser Trp Trp Asp Gln His Tyr Lys
    275                 280                 285
Trp Pro Tyr Pro Ser Glu Thr Gln Lys Val Ala Leu Ala Glu Ser Thr
        290                 295                 300
Gly Leu Asp Leu Lys Gln Ile Asn Asn Trp Phe Ile Asn Gln Arg Lys
305                 310                 315                 320
Arg His Trp Lys Pro Ser Glu Glu Met His His Leu Met Met Asp Gly
                325                 330                 335
Tyr His Thr Thr Asn Ala Phe Tyr Met Asp Gly His Phe Ile Asn Asp
        340                 345                 350
Gly Gly Leu Tyr Arg Leu Gly
        355

<210> SEQ ID NO 4
<211> LENGTH: 237
<212> TYPE: DNA
<213> ORGANISM: Artificial sequence
<220> FEATURE:
<223> OTHER INFORMATION: synthesized
<220> FEATURE:
<221> NAME/KEY: CDS
<222> LOCATION: (28)..(153)

<400> SEQUENCE: 4
aaaggttaac taagaagcaa tacttcc atg gat cca tgg agg aga tca ccc aac    54
                                Met Asp Pro Trp Arg Arg Ser Pro Asn
                                 1               5 act ttg gag ttg gcg caa gca gcc acg gcc atg gcc acg gcc agc acc   102
Thr Leu Glu Leu Ala Gln Ala Ala Thr Ala Met Ala Thr Ala Ser Thr
 10              15                  20                  25 acc atc atc acc acc acc acc acc cgt ggg cat cct ccc tca gcg ccg   150
Thr Ile Ile Thr Thr Thr Thr Thr Arg Gly His Pro Pro Ser Ala Pro
                 30                  35                  40 tcg tagcgccgct gccgccgcaa ccgccaagcg caggcctgcc gctgaccctg           203
Ser aacacggtgg cggccactgg aacagcggc ggta                                 237

<210> SEQ ID NO 5
<211> LENGTH: 42
<212> TYPE: PRT
<213> ORGANISM: Artificial sequence
<220> FEATURE:
<223> OTHER INFORMATION: Synthetic Construct

<400> SEQUENCE: 5

Met Asp Pro Trp Arg Arg Ser Pro Asn Thr Leu Glu Leu Ala Gln Ala
```

```
                1               5                  10                 15
Ala Thr Ala Met Ala Thr Ala Ser Thr Thr Ile Ile Thr Thr Thr Thr
                20                  25                 30

Thr Arg Gly His Pro Pro Ser Ala Pro Ser
        35                  40

<210> SEQ ID NO 6
<211> LENGTH: 237
<212> TYPE: DNA
<213> ORGANISM: Artificial sequence
<220> FEATURE:
<223> OTHER INFORMATION: synthesized
<220> FEATURE:
<221> NAME/KEY: CDS
<222> LOCATION: (36)..(236)

<400> SEQUENCE: 6
aaaggttaac taagaagcaa tacttccatg gatcc atg gag gag atc acc caa        53
                                     Met Glu Glu Ile Thr Gln
                                      1               5 cac ttt gga gtt ggc gca agc agc cac ggc cat ggc cac ggc cag cac      101
His Phe Gly Val Gly Ala Ser Ser His Gly His Gly His Gly Gln His
                10                  15                  20 cac cat cat cac cac cac cac cac ccg tgg gca tcc tcc ctc agc gcc      149
His His His His His His His His Pro Trp Ala Ser Ser Leu Ser Ala
            25                  30                  35 gtc gta gcg ccg ctg ccg ccg caa ccg cca agc gca ggc ctg ccg ctg      197
Val Val Ala Pro Leu Pro Pro Gln Pro Pro Ser Ala Gly Leu Pro Leu
        40                  45                  50 acc ctg aac acg gtg gcg gcc act ggg aac agc ggc ggt a                237
Thr Leu Asn Thr Val Ala Ala Thr Gly Asn Ser Gly Gly
    55                  60                  65

<210> SEQ ID NO 7
<211> LENGTH: 67
<212> TYPE: PRT
<213> ORGANISM: Artificial sequence
<220> FEATURE:
<223> OTHER INFORMATION: Synthetic Construct

<400> SEQUENCE: 7

Met Glu Glu Ile Thr Gln His Phe Gly Val Gly Ala Ser Ser His Gly
 1               5                  10                  15

His Gly His Gly Gln His His His His His His His His Pro Trp
                20                  25                  30

Ala Ser Ser Leu Ser Ala Val Val Ala Pro Leu Pro Pro Gln Pro Pro
            35                  40                  45

Ser Ala Gly Leu Pro Leu Thr Leu Asn Thr Val Ala Ala Thr Gly Asn
        50                  55                  60

Ser Gly Gly
65
```

METHODS AND COMPOSITIONS FOR ENHANCED YIELD BY TARGETED EXPRESSION OF KNOTTED1

CROSS REFERENCE

This utility application claims the benefit of U.S. Provisional Application Ser. No. 61/119,918, filed Dec. 4, 2008, which is incorporated herein by reference.

FIELD OF THE INVENTION

The invention relates to the field of genetic manipulation of plants, particularly the modulation of gene activity to affect yield in plants, particularly soybeans.

BACKGROUND OF THE INVENTION

The knotted1 (kn1) gene, originally isolated from maize by transposon tagging, encodes a nuclear homeodomain-containing transcription factor active in a regulatory network controlling the meristematic state of cells, which in turn regulates cell development and differentiation. Hake, et al., (1989) *EMBO J.* 8:15-22; Volbrecht, et al., (1991) *Nature* 350:241-243; Sinha, et al., 1993 *Genes and Development* 7:787-795. Knotted1 is the founding member of a family of homeodomain proteins conserved in higher plants. Homologues of knotted1 with conserved homeodomains have been isolated from a variety of species, including rice (Matsuoka, et al., (1993) *Plant Cell* 5:1039-1048), *Arabidopsis* (Ruberti, et al., (1991) *EMBO J.* 10:1787-1791; Mattsson, et al., (1992) *Plant Mol. Bio.* 18:1019-1022; Schena and David, (1992) *PNAS* 89:3894-3898; Lincoln, et al., (1994) *Plant Cell* 6:1859-1876), soybean (Ma, et al., (1994) *Plant Molecular Biology* 24:465-473), barley (Muller, et al., (1995) *Nature* 374:727-730), sorghum (Malcomber, et al., GenBank DQ317417) and wheat (Ishida and Takumi, GenBank AB465042). This class of proteins is characterized by a conservation of amino acid residues in the recognition helix and N-terminus of the homeodomain; further sequence homologies among kn1-related genes are found in the 24 amino acids immediately upstream of the homeodomain, referred to as the ELK region. Kerstetter, et al., (1994) *The Plant Cell* 6:1877-1887; Burglin, (1997) *Nucleic Acids Research* 25(21):4173-4180; Burglin, (1998) *Dev. Genes. Evol.* 108:113-116.

Tobacco plants expressing maize Kn1 under a strong constitutive promoter displayed a range of altered phenotypes generally including malformed leaves, shortened internodes, loss of apical dominance and the formation of epiphyllic shoots. Sinha, et al., (1993) *Genes and Development* 7:787-795. Phenotypic similarity between cytokinin-overproducing *Arabidopsis* and Kn1-overexpressing plants suggested that a single pathway is involved and that cytokinins may act upstream of kn1, inducing its expression. Rupp, et al., (1999) *Plant Journal* 18(5):557-563. However, expression of maize kn1 in tobacco, under control of the senescence-associated SAG12 promoter, delayed leaf senescence and increased leaf cytokinin content by as much as 15-fold. Ori, et al., (1999) *Plant Cell* 11:1073-1080. Thus, kn1 expression and cytokinin levels may positively regulate each other in a complex interdependency. D'Agostino and Kieber, (1999) *Current Opinions in Plant Biology* 2:359-364. The KN1 homeodomain proteins may play pivotal roles in maintaining leaf cells in an indeterminate state. Immunolocalization studies have demonstrated that the KN1 protein is nuclear and thus consistent with the predicted function of kn1 gene as a transcription factor.

The KN1-type homeodomain proteins have been subdivided into two groups, classes 1 and 2 (Kerstetter, et al., 1994). Class 1 includes the maize kn1 gene. The class 1 products share extensive amino acid identity in the homeodomain and in general, they are strongly expressed around the shoot meristem, moderately to weakly expressed in the embryo and/or other restricted tissues and barely expressed in differentiated organs, such as leaves and roots (Kerstetter, et al., 1994). Ectopic expression of kn1-like class 1 genes has been reported to cause altered leaf and flower morphology in spontaneous mutants of a number of plant species (Liu, et al., (2008) *Journal of Genetics and Genomics* 35:441-449; Smith, et al., (1992) *Development* 116:21-30; Chen, et al., (1997); Parnis, et al., (1997)) and in transgenic plants (Matsuoka, et al., (1993) *Plant Cell* 5:1039-1048; Lincoln, et al., (1994) *Plant Cell* 6:1859-1876). The class 2 genes, which are comparatively less similar to maize kn1 in their homeodomains, are expressed in most tissues at different levels, depending upon the tissue. In contrast to the class 1 genes, overexpression of class 2 genes in transgenic plants does not cause altered morphology.

Cytokinins are a class of $N^6$ substituted purine derivative plant hormones that regulate cell division and influence a large number of developmental events, such as shoot development, sink strength, root branching, control of apical dominance in the shoot, leaf development, chloroplast development and leaf senescence (Mok, et al., (1994) *Cytokinins. Chemistry, Action and Function*. CRC Press, Boca Raton, FLA, pp. 155-166; Horgan, (1984) *Advanced Plant Physiology* ed. MB., Pitman, London, UK, pp 53-75 and Letham, (1994) *Annual Review of Plant Physiol* 34:163-197). In maize, cytokinins (CK) play an important role in establishing seed size, decreasing tip kernel abortion and increasing seed set during unfavorable environmental conditions (Cheikh, et al., (1994) *Plant Physiol.* 106:45-51; Dietrich, et al., (1995) *Plant Physiol Biochem* 33:327-36). Active cytokinin pools are regulated by rates of synthesis and degradation.

Until recently, roots were believed to be the major site of cytokinin biosynthesis but evidence indicates that others tissues, such as shoot meristems and developing seeds, also have high cytokinin biosynthetic activity. It has been suggested that cytokinins are synthesized in restricted sites where cell proliferation is active. The presence of several Atipt genes in *Arabidopsis* and their differential pattern of expression might serve this purpose.

The enzyme isopentenyl transferase (IPT) directs the synthesis of cytokinins and plays a major role in controlling cytokinin levels in plant tissues. Multiple routes have been proposed for cytokinin biosynthesis. Transfer RNA degradation has been suggested to be a source of cytokinin, because some tRNA molecules contain an isopentenyladenosine (iPA) residue at the site adjacent to the anticodon (Swaminathan, et al., (1977) *Biochemistry* 16:1355-1360). The modification is catalyzed by tRNA isopentenyl transferase (tRNA IPT; EC 2.5.1.8), which has been identified in various organisms such as *Escherichia coli, Saccharomyces cerevisiae, Lactobacillus acidophilus, Homo sapiens* and *Zea mays* (Bartz, et al., (1972) *Biochemie* 54:31-39; Kline, et al., (1969) *Biochemistry* 8:4361-4371; Holtz, et al., (1975) *Hoppe-Seyler's Z Physiol. Chem.* 356:1459-1464; Golovko, et al., (2000) *Gene* 258:85-93 and Holtz, et al., (1979) *Hoppe-Seyler's Z Physiol. Chem.* 359:89-101). However, this pathway is not considered to be the main route for cytokinin synthesis (Chen, et al., (1997) *Physiol. Plant* 101:665-673 and McGraw, et al., (1995) *Plant Hormones, Physiology, Biochemistry and Molecular Biology* Ed. Davies, 98-117, Kluwer Academic Publishers, Dordrecht).

Another possible route of cytokinin formation is de novo biosynthesis of iPMP by adenylate isopentenyl transferase (IPT; EC 2.5.1.27) with dimethylallyl-diphosphate (DMAPP), AMP, ATP and ADP as substrates. Current knowledge of cytokinin biosynthesis in plants is largely deduced from studies on a possible analogous system in *Agrobacterium tumefaciens*. Cells of *A. tumefaciens* are able to infect certain plant species by inducing tumor formation in host plant tissues (Van Montagu, et al., (1982) *Curr Top Microbiol Immunol* 96:237-254; Hansen, et al., (1999). *Curr Top Microbiol Immunol* 240:21-57). To do so, the *A. tumefaciens* cells synthesize and secrete cytokinins which mediate the transformation of normal host plant tissues into tumors or calli. This process is facilitated by the *A. tumefaciens* tumor-inducing plasmid which contains genes encoding the necessary enzyme and regulators for cytokinin biosynthesis. Biochemical and genetic studies revealed that Gene 4 of the tumor-inducing plasmid encodes an isopentenyl transferase (IPT), which converts AMP and DMAPP into isopentenyladenosine-5'-monophosphate (iPMP), the active form of cytokinins (Akiyoshi, et al., (1984) *Proc. Natl. Acad. Sci. USA* 81:5994-5998). Overexpression of the *Agrobacterium* ipt gene in a variety of transgenic plants has been shown to cause an increased level of cytokinins and elicit typical cytokinin responses in the host plant (Hansen, et al., (1999) *Curr Top Microbiol Immunol* 240:21-57). Therefore, it has been postulated that plant cells use machinery similar to that of *A. tumefaciens* cells for cytokinin biosynthesis. Homologs of ipt have recently been identified in *Arabidopsis* and *Petunia hybrida* (Takei, et al., (2001) *J. Biol. Chem.* 276:26405-26410 and Kakimoto, (2001) *Plant Cell Physiol.* 42:677-685). Overexpression of the *Arabidopsis* ipt homologs in plants elevated cytokinin levels and elicited typical cytokinin responses in planta and under tissue culture conditions (Kakimoto, (2001) *Plant Cell Physiol.* 42:677-685).

*Arabidopsis* ipt genes are members of a small multigene family of nine different genes, two of which code for tRNA isopentenyl transferases and seven of which encode a gene product with a cytokinin biosynthetic function. Biochemical analysis of the recombinant AtIPT4 protein showed that, in contrast to the bacterial enzyme, the *Arabidopsis* enzyme uses ATP as a substrate instead of AMP. Another plant ipt gene (Sho) was identified in *Petunia hybrida* using an activation tagging strategy (Zubko, et al., (2002) *The Plant Journal* 29:797-808).

Regarding cytokinin biosynthesis and effect, see, for example, Ahikari, et al., (2005) *Science* 309:741-745; Cho, et al., (2002) *Plant Growth Reg* 36(3):215-221; Dietrich, et al., (1995) *Plant Physiol. Biochem* 33(3):327-336; Kaminek, (1992) *Trends Biotech* 10:159-164; Kokobun and Honda, (2000) *Plant Prod. Sci.* 3:354-359; Nagel, et al., (2001) *Annals Bot.* 88(1):27-31; Yashima, et al., (2005) *Plant Prod. Sci.* 8(2):139-144.

In view of the influence of cytokinins on a wide variety of plant developmental processes, including root architecture, shoot and leaf development and seed set, the ability to manipulate cytokinin levels in higher plant cells, and thereby drastically effect plant growth and productivity, offers significant commercial value (Mok, et al., (1994) *Cytokinins. Chemistry, Action and Function*. CRC Press, Boca Raton, Fla., pp. 155-166). The modulation of cytokinin, however, due to the many effects it has on plants and the multiple pathways for regulation and synthesis, is a complex process requiring careful temporal and spatial regulation in transgenic plants.

As can be seen, a continuing need exists for methods of modulation and characterization of developmental pathways for positively affecting crop plant yield.

BRIEF SUMMARY OF THE INVENTION

The maize transcription factor knotted1 (aka Kn1, kn1, KN1 or KNOTTED1) is involved in maintaining the meristematic state of cells, which in turn regulates cell development and differentiation. Prior work by the Applicants demonstrated that constitutive over-expression of kn1 in corn and soybean plants created deleterious phenotypes, including a knotted-leaf phenotype in both species. In soybean, constitutive overexpression of kn1 in soybean also resulted in plants with enlarged leaves on smaller petioles and a negative impact on final seed yield (Applicants; data not shown). According to the invention, regulated knotted1 expression, preferentially targeted to reproductive structures during flowering and/or seed development, creates a sequestered transcription factor effect, and results in plants with increased yield, which may be due to reduced abortion of flowers, pods, and/or seeds. In light of the strong negative pleiotropy observed to result from overexpression of kn1 in several species, as described above, and the potential for compounded downstream effects when transcription factor expression is modulated, the invention provides surprising positive results via use of novel expression constructs which appropriately target kn1 overexpression.

In one embodiment, the soy annexin (ann) promoter, which targets gene expression to developing reproductive structures, is operably linked to knotted1 to create a targeted expression construct which increases yield.

Compositions and methods of the invention comprise and employ modulation of knotted1 (kn1) polypeptides and polynucleotides that are postulated to be involved with cytokinin production or other genes modulating plant development, morphology and physiology. Ectopic expression of kn1 in a targeted manner may increase localized cytokinin synthesis or activity. Without being limited to any particular mode of action, Applicants provide constructs and methods for improved seed yield.

Compositions further include expression cassettes, plants, plant cells and seeds having the regulatory elements and kn1 sequences for carefully modulated, temporally- and/or spatially-regulated expression of the same. Expression is preferentially targeted to the developing seed and/or flower. The plants, plant cells and seeds of the invention may exhibit phenotypic changes, such as modulated (increased or decreased) cytokinin levels; modulated floral development; modulated pod or ear development; modulated root development; altered shoot-to-root ratio; increased seed size or an increased seed weight; increased plant yield or plant vigor; maintained or improved stress tolerance (e.g., increased or unchanged size of the plant, minimized seed and/or pod abortion, increased or unchanged seed set, all under stress conditions); modulated shoot growth; delayed senescence or an enhanced vegetative growth, all relative to a plant, plant cell or seed not modified per the invention.

Methods are provided for reducing or eliminating the activity of a kn1 polypeptide in a plant, comprising introducing into the plant a selected polynucleotide. In specific methods, providing the polynucleotide may decrease the level of cytokinin in the plant and/or modulate leaf, flower and/or pod development of the plant.

Methods are also provided for increasing the level of a kn1 polypeptide in a plant at specifically regulated times and tissues comprising introducing into the plant a selected polynucleotide with appropriate regulatory elements. In specific methods, expression of the kn1 polynucleotide may increase the level of cytokinin in the plant and has been demonstrated to modulate flower and pod development, increasing yield and possibly decreasing abortion of flowers, pods and/or seeds. Modulated expression of this transcription factor may also have other developmental effects which include maintaining or increasing the size of the plant; minimizing seed abortion; increasing or maintaining seed set; increasing shoot growth; increasing seed size or seed weight; increasing plant yield or plant vigor; modulating floral development; delaying senescence or increasing leaf growth. Increase in kn1 expression is directed spatially and/or timed developmentally to seed production, flower development and/or reproductive tissues generally.

BRIEF DESCRIPTION OF THE DRAWINGS

FIG. 2 shows features of PHP24677A and their location within SEQ ID NO: 1.

FIG. 3 shows an overlapping ORF in PHP24677 (see SEQ ID NOs: 4 and 5).

FIG. 5 shows that transgene-positive seeds have significantly higher cytokinin levels.

FIG. 8 shows features of PHP35999A and their location within SEQ ID NO: 2.

BRIEF DESCRIPTION OF THE SEQUENCES

Figure 4:
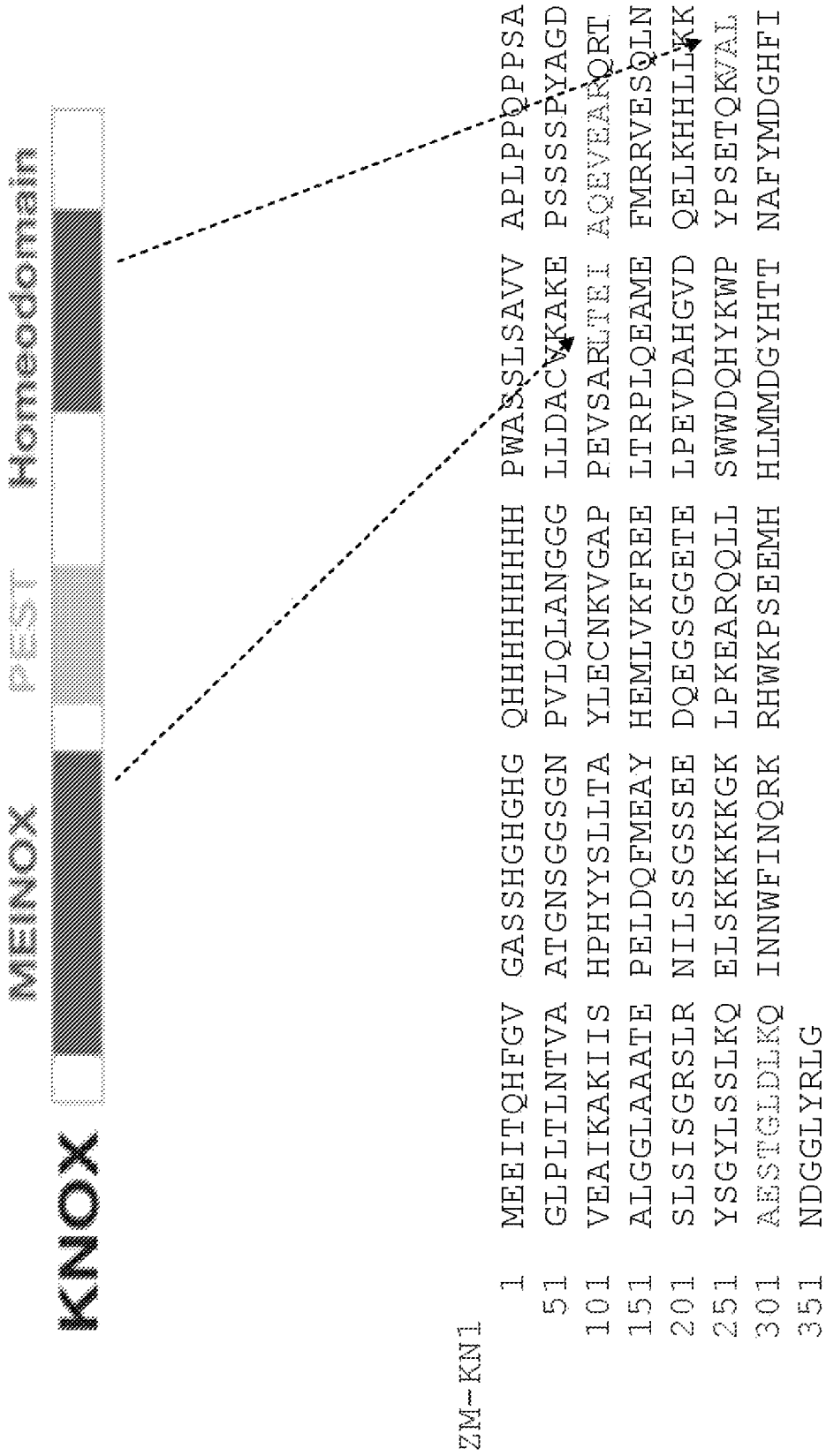
FIG. 4 shows the location of mass-spectrometry tags within the sequence of the kn1 polypeptide (see SEQ ID NO: 3).

SEQ ID NO: 1 is the sequence of PHP24677A.
SEQ ID NO: 2 is the sequence of PHP35999A.
SEQ ID NO: 3 is the amino acid sequence of FIG. 4.
SEQ ID NO: 4 is the nucleotide sequence of FIG. 3.
SEQ ID NO: 5 is the amino acid sequence encoded by the ORF which begins at position 28 of FIG. 3.
SEQ ID NO: 6 is the nucleotide sequence of FIG. 3.
SEQ ID NO: 7 is the amino acid sequence encoded by the ORF which begins at position 36 of FIG. 3.

DETAILED DESCRIPTION OF THE INVENTION

According to the invention, ectopic expression of kn1 is regulated to create a sequestered effect. Expression of the kn1 gene targeted preferentially to developing flowers and seeds (or other reproductive structures) is shown to improve yield of the resultant plant and may decrease abortion of flowers, pods and/or seeds.

The present invention now will be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements.

Many modifications and other embodiments of the invention set forth herein will come to mind to one skilled in the art to which this invention pertains, having the benefit of the teachings presented in the descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation. All references cited herein are hereby incorporated in their entirety by reference.

Compositions

Compositions of the invention include Knotted1 polypeptides and polynucleotides that are involved in modulating plant development, morphology and physiology. The compositions include polynucleotides which are operably linked to regulatory sequences for targeted expression of the same. In particular, the present invention provides for isolated polynucleotides comprising, for example a maize knotted1 nucleotide sequence as indicated in SEQ ID NO: 1 and FIG. 2.

The kn1 polypeptides for use in the invention share sequence identity with members of the homeobox family of proteins particularly, class I.

As used herein, the term "knotted1", "KNOTTED1", "KN1", "Kn1" and kn1", in italicized or standard format, shall be used interchangeably and shall be interpreted to include either the polynucleotide sequence encoding the transcription factor or the protein, unless one or the other is specified and shall include any member of the family of knotted homeobox transcription factors generally associated with the knotted leaf phenotype upon overexpression and as exemplified herein. As discussed, supra, these transcription factors will likely share a similar ELK region and conserved homeodomain. Several such factors are known in the art such as kn1 from maize (GenBank Accession Numbers X61308 and X57672 and SEQ ID NO: 2); Osh1 and OSH45B from rice, (GenBank Accession Numbers D16507 and D49704); Sbh1 from Soybean (GenBank Accession Number L13663); KNAT1, KNAT2, KNAT3, KNAT4, KNAT6, and STM from *Arabidopsis* (GenBank Accession Numbers U14174, U14175, X92392, X92393 (NM102187 and NM 180620 for KNAT 6) and U32344); BNHD1 from *Brassica napus* (GenBank Accession Number Z29073); HVKNOX3 from *Hordeum vulgare* (GenBank Accession Number X83518); LET6, LET12, LETKN1 from *Lycopersicon esculentum* (GenBank Accession Numbers AF000141, AF000142, U32247); PAHBK1 and ZMRS1 from *Picea abies* (Sundas-Larsson, et. al., (1998) and GenBank Accession Number L44133); knotted1, NTH1, NTH15 and NTH23 from *Nicotiana tabacum* (GenBank Accession Numbers AF544052, AB025573, AB004785 and AB004797).

While not wishing to be bound by any theory, Applicants postulate that the knotted1 transcription factors are involved in cytokinin biosynthesis and that the kn1 polypeptides of the invention have "cytokinin synthesis activity." By "cytokinin synthesis activity" is intended enzymatic activity that generates cytokinins, derivatives thereof or any intermediates in the cytokinin synthesis pathway. Cytokinin synthesis activity therefore includes, but is not limited to, DMAPP:AMP isopentenyltransferase activity (the conversion of AMP (adenosine-5'-monophosphate) and DMAPP into iPMP (isopentenyladenosine-5'-monophosphate)), DMAPP:ADP isopentenyltransferase activity (the conversion of ADP (adenosine-5'-diphosphate) and DMAPP into iPDP (isopentenyladenosine-5'-diphosphate)); DMAPP:ATP isopentenyltransferase activity (the conversion of ATP (adenosine-5'-triphosphate) and DMAPP into iptP (isopentenyladenosine-5'-triphosphate)) and DMAPP:tRNA isopentenyltransferase activity (the modification of cytoplasmic, chloroplastic and/or mitochondrial tRNAs to give isopentenyl). Cytokinin synthesis activity can further include a substrate comprising a second side chain precursor, other than DMAPP. Examples of side chain donors include compounds of terpenoid origin. For example, the substrate could be hydroxymethylbutenyl diphosphate (HMBPP) which would allow trans-zeatin riboside monophosphate (ZMP) synthesis. See, for example, Åstot, et al., (2000) *Proc Natl Acad Sci* 97:14778-14783 and Takei, et al., (2003) *J Plant Res.* 116(3):265-9.

Cytokinin synthesis activity further includes the synthesis of intermediates involved in formation of ZMP. Methods to assay for the production of various cytokinins and their intermediates can be found, for example, in Takei, et al., (2001) *The Journal of Biological Chemistry* 276:26405-26410, Zubo, et al., (2002) *The Plant Journal* 29:797-808; Kakimoto, et al., (2001) *Plant Cell Physio.* 42:677-658 and Sun, et al., (2003) *Plant Physiology* 131:167-176, each of which is herein incorporated by reference. "Cytokinin synthesis activity" also includes any alteration in a plant or plant cell phenotype that is characteristic of an increase in cytokinin concentration. Such cytokinin specific effects are discussed elsewhere herein and include, but are not limited to, enhanced shoot formation, reduced apical dominance, delayed senescence, increased leaf growth, increased cytokinin levels in the plant, increased tolerance to stress, minimization of pod and/or seed abortion and increased or maintained seed set under optimal or stress conditions. Assays to measure or detect such phenotypes are known. See, for example, Miyawaki, et al., (2004) *The Plant Journal* 37:128-138, Takei, et al., (2001) *The Journal of Biological Chemistry* 276:26405-26410, Zubo, et al., (2002) *The Plant Journal* 29:797-808; Kakimoto, et al., (2001) *Plant Cell Physio.* 42:677-658 and Sun, et al., (2003) *Plant Physiology* 131:167-176, each of which is herein incorporated by reference. Additional phenotypes resulting from an increase in cytokinin synthesis activity in a plant are discussed herein.

Compositions of the invention include kn1 sequences which may be involved in cytokinin biosynthesis or in activation of genes involved in metabolic processes that lead to increased floral and/or pod retention, seed set and/or yield. In particular, the present invention provides for isolated polynucleotides comprising nucleotide sequences as set forth in SEQ ID NO: 1. Further provided are polypeptides having an amino acid sequence encoded by a polynucleotide described herein, for example those set forth in SEQ ID NO: 1 and fragments and variants thereof.

The invention encompasses isolated or substantially purified polynucleotide or protein compositions. An "isolated" or "purified" polynucleotide or protein or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques or substantially free of chemical precursors or other chemicals when chemically synthesized. Optimally, an "isolated" polynucleotide is free of sequences that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flanks the polynucleotide in genomic DNA of the cell from which the polynucleotide is derived. A protein that is substantially free of cellular material includes preparations of protein having less than about 30%, 20%, 10%, 5% or 1% (by dry weight) of contaminating protein. When the protein of the invention or biologically active portion thereof is recombinantly produced, optimally culture medium represents less than about 30%, 20%, 10%, 5% or 1% (by dry weight) of chemical precursors or non-protein-of-interest chemicals.

Fragments and variants of the disclosed polynucleotides and proteins encoded thereby are also encompassed by the present invention. "Fragment" is intended to mean a portion of the polynucleotide or a portion of the amino acid sequence and hence of the protein encoded thereby. Fragments of a polynucleotide may encode protein fragments that retain the biological activity of the native protein and hence have cytokinin synthesis activity or induce other metabolic changes. Alternatively, fragments of a polynucleotide that are useful as hybridization probes generally do not encode proteins retaining biological activity. Thus, fragments of a nucleotide sequence may range from at least about 20 nucleotides, about 50 nucleotides, about 100 nucleotides and up to the full-length polynucleotide encoding a protein of the invention.

A fragment of a kn1 polynucleotide that encodes a biologically active portion of a kn1 protein of the invention will encode at least 15, 25, 30, 50, 100, 150, 200, 225, 250, 275, 300, 310, 315 or 320 contiguous amino acids or up to the total number of amino acids present in a full-length KN1 protein of the invention. Fragments of a kn1 polynucleotide that are useful as hybridization probes or PCR primers generally need not encode a biologically active portion of a KN1 protein.

Thus, a fragment of a kn1 polynucleotide may encode a biologically active portion of a KN1 protein or it may be a fragment that can be used as a hybridization probe or PCR primer using methods disclosed below. A biologically active portion of a KN1 protein can be prepared by isolating a portion of one of the kn1 polynucleotides of the invention, expressing the encoded portion of the KN1 protein (e.g., by recombinant expression in vitro) and assessing the activity of the encoded portion of the KN1 protein. Polynucleotides that are fragments of a kn1 nucleotide sequence comprise at least 16, 20, 50, 75, 100, 150, 200, 250, 300, 350, 400, 450, 500, 550, 600, 650, 700, 800, 900, 950 or 965 contiguous nucleotides or up to the number of nucleotides present in a full-length kn1 polynucleotide disclosed herein.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the kn1 polypeptides of the invention. Naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a KN1 protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to a kn1 polypeptide encoded by a portion of SEQ ID NO: 1 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more sites in the native protein and/or substitution of one or more amino acids at one or more sites in the native protein. Certain variant proteins encompassed by the present invention are biologically active, that is they continue to possess the desired biological activity of the native protein, that is, cytokinin synthesis activity, as described herein. Such variants may result from, for example, genetic polymorphism or from human manipulation. Biologically active variants of a native KN1 protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2 or even 1 amino acid residue.

The proteins of the invention may be altered in various ways including amino acid substitutions, deletions, truncations and insertions. Methods for such manipulations are generally known in the art. For example, amino acid sequence variants and fragments of the KN1 proteins can be prepared by mutations in the DNA. Methods for mutagenesis and polynucleotide alterations are well known in the art. See, for example, Kunkel, (1985) *Proc. Natl. Acad. Sci USA* 82:488-492; Kunkel, et al., (1987) *Methods in Enzymol.* 154:367-382; U.S. Pat. No. 4,873,192; Walker and Gaastra, eds. (1983) *Techniques in Molecular Biology* (MacMillan Publishing Company, New York), and the references cited therein. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass naturally occurring proteins as well as variations and modified forms thereof. Such variants will continue to possess the desired KN1 activity. Obviously, the mutations that will be made in the DNA encoding the variant must not place the sequence out of reading frame and optimally will not create complementary regions that could produce secondary mRNA structure.

The deletions, insertions and substitutions of the protein sequences encompassed herein are not expected to produce radical changes in the characteristics of the protein. However, when it is difficult to predict the exact effect of the substitution, deletion or insertion in advance of doing so, one skilled in the art will appreciate that the effect will be evaluated by routine screening assays. That is, the activity can be evaluated by assaying for cytokinin synthesis activity. See, for example, Takei, et al., (2001) *The Journal of Biological Chemistry* 276:26405-26410; Zubo, et al., (2002) *The Plant Journal* 29:797-808; Kakimoto, et al., (2001) *Plant Cell Physio.* 42:677-658; Sun, et al., (2003) *Plant Physiology* 131:167-176 and Miyawaki, et al., (2004) *The Plant Journal* 37:128-138, all of which are herein incorporated by reference.

Variant polynucleotides and proteins also encompass sequences and proteins derived from a mutagenic and recombinogenic procedure such as DNA shuffling. With such a procedure, one or more different kn1 coding sequences can be manipulated to create a new kn1 polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the kn1 gene of the invention and other known kn1 genes to obtain a new gene coding for a protein with an improved property of interest, such as an increased $K_m$ in the case of an enzyme. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; PCT Publication Number WO 97/20078 and U.S. Pat. Nos. 5,605,793 and 5,837,458.

By "promoter" is intended a regulatory region of DNA usually comprising a TATA box capable of directing RNA polymerase II to initiate RNA synthesis at the appropriate transcription initiation site for a particular polynucleotide sequence. A promoter may additionally comprise other recognition sequences generally positioned upstream or 5' to the TATA box, referred to as upstream promoter elements, which influence the transcription initiation rate. The promoter sequences of the present invention regulate (i.e., repress or activate) transcription.

The polynucleotides of the invention can be used to isolate corresponding sequences from other organisms, particularly other plants, more particularly other monocots or dicot species. In this manner, methods such as PCR, hybridization and the like can be used to identify such sequences based on their sequence homology to the sequences set forth herein. Sequences isolated based on their sequence identity to the entire kn1 sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99% or greater sequence identity. Functions of orthologs are often highly conserved among species. Thus, isolated polynucleotides that encode a kn1 protein and which hybridize under stringent conditions to the kn1 sequences disclosed herein or to variants or fragments or complements thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also, Innis, et al., eds. (1990) *PCR Protocols: A Guide to Methods and Applications* (Academic Press, New York); Innis and Gelfand, eds. (1995) *PCR Strategies* (Academic Press, New York) and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments or other oligonucleotides and may be labeled with a detectable group such as $^{32}P$, or any other detectable marker. Thus, for example, probes for hybridization can be made by labeling synthetic oligonucleotides based on the kn1 polynucleotides of the invention. Methods for preparation of probes for hybridization and for construction of cDNA and genomic libraries are generally known in the art and are disclosed in Sambrook, et al., (1989) *Molecular Cloning: A Laboratory Manual* (2d ed., Cold Spring Harbor Laboratory Press, Plainview, N.Y.).

For example, an entire kn1 polynucleotide disclosed herein or one or more portions thereof, may be used as a probe capable of specifically hybridizing to corresponding kn1 polynucleotides. To achieve specific hybridization under a variety of conditions, such probes include sequences that are unique among kn1 polynucleotide sequences and are optimally at least about 10 nucleotides in length and most optimally at least about 20 nucleotides in length. Such probes may be used to amplify corresponding kn1 polynucleotides from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Plainview, N.Y.). Hybridization of such sequences may be carried out under stringent conditions.

By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.* 138:267-284: $T_m=81.5°$ C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen, (1993) *Laboratory Techniques in Biochemistry and Molecular Biology—Hybridization with Nucleic Acid Probes*, Part I, Chapter 2 (Elsevier, N.Y.) and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) *CABIOS* 4:11-17; the local alignment algorithm of Smith, et al., (1981) *Adv. Appl. Math.* 2:482; the global alignment algorithm of Needleman and Wunsch, (1970) *J. Mol. Biol.* 48:443-453; the search-for-local alignment method of Pearson and Lipman, (1988) *Proc. Natl. Acad. Sci* 85:2444-2448; the algorithm of Karlin and Altschul, (1990) *Proc. Natl. Acad. Sci USA* 872264, modified as in Karlin and Altschul, (1993) *Proc. Natl. Acad. Sci USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA and TFASTA in the GCG Wisconsin Genetics Software Package®, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65 and Pearson, et al., (1994) *Meth. Mol. Biol.* 24:307-331. The ALIGN program is based on the algorithm of Myers and Miller, (1988) supra. A PAM120 weight residue table, a gap length penalty of 12 and a gap penalty of 4 can be used with the ALIGN program when comparing amino acid sequences. The BLAST programs of Altschul, et al., (1990) *J. Mol. Biol.* 215:403 are based on the algorithm of Karlin and Altschul, (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2 and the BLOSUM62 scoring matrix.

GAP uses the algorithm of Needleman and Wunsch, (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package® for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package® is BLOSUM62 (see, Henikoff and Henikoff, (1989) *Proc. Natl. Acad. Sci. USA* 89:10915).

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The invention further provides plants having altered levels and/or activities of a kn1 polypeptide of the invention. In some embodiments, the plants of the invention have stably incorporated into their genome a kn1 sequence of the invention. In other embodiments, plants that are genetically modified at a genomic locus encoding a kn1 polypeptide of the invention are provided. By "native genomic locus" is intended a naturally occurring genomic sequence. The genomic locus may be modified to reduce or eliminate the activity of the kn1 polypeptide. The term "genetically modified" as used herein refers to a plant or plant part that is modified in its genetic information by the introduction of one or more foreign polynucleotides and the insertion of the foreign polynucleotide leads to a phenotypic change in the plant. By "phenotypic change" is intended a measurable change in one or more cell functions. For example, plants having a genetic modification at the genomic locus encoding the kn1 polypeptide can show reduced or eliminated expression or activity of the kn1 polypeptide. Various methods to generate such a genetically modified genomic locus are described elsewhere herein, as are the variety of phenotypes that can result from the modulation of the level/activity of the kn1 sequences of the invention.

As used herein, the term plant includes reference to whole plants, plant parts or organs (e.g., leaves, stems, roots), plant cells and seeds and progeny of same. Plant cell, as used herein, includes, without limitation, cells obtained from or found in seeds, suspension cultures, embryos, meristematic regions, callus tissue, leaves, roots, shoots, gametophytes, sporophytes, pollen and microspores, as well as plant protoplasts and plant cell tissue cultures, plant calli, plant clumps and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, "grain" refers to the mature seed produced by commercial growers for purposes other than growing or reproducing the species. Progeny, variants and mutants of the regenerated plants are also included within the scope of the invention, provided that these parts comprise the introduced nucleic acid sequences.

Methods

I. Providing Sequences

The kn1 sequences of the present invention can be introduced into and expressed in a host cell such as bacteria, yeast, insect, mammalian or optimally plant cells. These sequences are known to those of skill in the art and available to the same through sources such as GenBank. It is expected as well that those of skill in the art are knowledgeable in the numerous systems available for the introduction of a polypeptide or a nucleotide sequence of the present invention into a host cell. No attempt to describe in detail the various methods known for providing proteins in prokaryotes or eukaryotes will be made.

By "host cell" is meant a cell which comprises a heterologous nucleic acid sequence of the invention. Host cells may be prokaryotic cells such as *E. coli* or eukaryotic cells such as yeast, insect, amphibian or mammalian cells. Host cells can also be monocotyledonous or dicotyledonous plant cells. In certain embodiments, the dicotyledonous host cell is a soybean host cell.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

According to the invention, a kn1 polynucleotide may be provided in an expression cassette for expression in the plant of interest. The cassette will include 5' and 3' regulatory sequences operably linked to a kn1 polynucleotide. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. An expression cassette may be provided with a plurality of restriction sites and/or recombination sites for insertion of the kn1 polynucleotide to be under the transcriptional regulation of the regulatory regions. The expression cassette may additionally contain selectable marker genes.

In certain embodiments, the expression cassette will include in the 5'-3' direction of transcription, a transcriptional and translational initiation region (i.e., a promoter), a kn1 polynucleotide and a transcriptional and translational termination region (i.e., termination region) functional in plants. The regulatory regions (i.e., promoters, transcriptional regulatory regions, and translational termination regions) and/or the kn1 polynucleotide of the invention may be native/analogous to the host cell or to each other. Alternatively, the regulatory regions and/or the kn1 polynucleotide may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/ analogous species, one or both are substantially modified from their original form and/or genomic locus or the promoter is not the native promoter for the operably-linked polynucleotide. As used herein, a chimeric gene comprises a coding sequence operably linked to a transcription initiation region that is heterologous to the coding sequence.

While heterologous promoters can be used to express the kn1 sequences, the native promoter sequences or other kn1 promoters may also be used. Such constructs can change expression levels of kn1 sequences in the plant or plant cell. Thus, the phenotype of the plant or plant cell can be altered.

The termination region may be native with the transcriptional initiation region, may be native with the operably-linked kn1 polynucleotide of interest, may be native with the plant host or may be derived from another source (i.e., foreign or heterologous with reference to the promoter, the kn1 polynucleotide of interest, the plant host or any combination thereof). Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri, (1990) *Plant Physiol.* 92:1-11 for a discussion of host-preferred codon usage. Methods are available in the art for synthesizing plant-preferred genes. See, for example, U.S. Pat. Nos. 5,380,831 and 5,436,391 and Murray, et al., (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus) (*Virology* 154:9-20) and human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Other methods known to enhance translation can also be utilized.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as chlorsulfuron (2-chloro-N-[(4-methoxy-6-methyl-1,3,5-triazin-2-yl) aminocarbonyl]-benzenesulfonamide), glufosinate ammonium, bromoxynil, imidazolinones and 2,4-dichlorophenoxyacetate (2,4-D). Additional selectable markers include phenotypic markers such as β-galactosidase and fluorescent proteins such as green fluorescent protein (GFP) (Su, et al., (2004) *Biotechnol Bioeng* 85:610-9 and Fetter, et al., (2004) *Plant Cell* 16.215-28), cyan fluorescent protein (CYP) (Bolte, et al., (2004) *J. Cell Science* 117:943-54 and Kato, et al., (2002) *Plant Physiol* 129:913-42) and yellow fluorescent protein (PhiYFP™ from Evrogen, see, Bolte, et al., (2004) *J. Cell Science* 117:943-54). For additional selectable markers, see generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Aci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Bairn, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology, Vol.* 78 (Springer-Verlag, Berlin); Gill, et al., (1988) *Nature* 334:721-724. Such disclosures are herein incorporated by reference. The above list of selectable marker genes is not meant to be limiting. Any selectable marker gene can be used in the present invention.

A number of promoters can be used in the practice of the invention, including the native promoter of the polynucleotide sequence of interest. The promoters can be selected based on the desired outcome. The nucleic acids can be combined with constitutive, inducible, tissue-preferred or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor.*

Appl. Genet. 81:581-588); MAS (Velten, et al., (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142 and 6,177,611.

Tissue-preferred promoters can be utilized to target enhanced kn1 expression within a particular plant tissue. Tissue-preferred promoters include Yamamoto, et al., (1997) *Plant J.* 12(2):255-265; Kawamata, et al., (1997) *Plant Cell Physiol.* 38(7):792-803; Hansen, et al., (1997) *Mol. Gen. Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) Plant Cell Physiol. 35(5):773-778; Lam (1994) *Results Probl. Cell Differ.* 20:181-196; Orozco, et al., (1993) *Plant Mol. Biol.* 23(6): 1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for lower expression. See, also, US Patent Application Publication Number 2003/0074698, herein incorporated by reference.

"Seed-preferred" promoters refers to those promoters active during seed development and may include expression in seed initials or related maternal tissue. Such seed-preferred promoters include, but are not limited to, Cim1 (cytokinin-induced message); cZ19B1 (maize 19 kDa zein); milps (myo-inositol-1-phosphate synthase) (see, WO 00/11177 and U.S. Pat. No. 6,225,529, herein incorporated by reference). Gamma-zein is an endosperm-specific promoter. Globulin-1 (Glob-1) is a representative embryo-specific promoter. For dicots, seed-specific promoters include, but are not limited to, bean β-phaseolin, napin, β-conglycinin, soybean lectin, cruciferin, sucrose synthase, P34 (US Patent Application Publication Number 2007/0033673), and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also, WO 00/12733, where seed-preferred promoters from end1 and end2 genes are disclosed, herein incorporated by reference. Additional embryo specific promoters are disclosed in Sato, et al., (1996) *Proc. Natl. Acad. Sci.* 93:8117-8122; Nakase, et al., (1997) *Plant J* 12:235-46 and Postma-Haarsma, et al., (1999) *Plant Mol. Biol.* 39:257-71. Additional endosperm specific promoters are disclosed in Albani, et al., (1984) *EMBO* 3:1405-15; Albani, et al., (1999) *Theor. Appl. Gen.* 98:1253-62; Albani, et al., (1993) *Plant J.* 4:343-55; Mena, et al., (1998) *The Plant Journal* 116:53-62 and Wu, et al., (1998) *Plant Cell Physiology* 39:885-889.

Also of interest are promoters active in meristem regions, such as developing inflorescence tissues, and promoters which drive expression at or about the time of anthesis or early kernel development. This may include, for example, the maize Zag promoters, including Zag1 and Zag2 (see, Schmidt, et al., (1993) *The Plant Cell* 5:729-37; GenBank X80206; Theissen, et al., (1995) *Gene* 156:155-166 and U.S. patent application Ser. No. 10/817,483); maize Zap promoter (also known as, ZmMADS; U.S. patent application Ser. No. 10/387,937; WO 03/078590); maize ckx1-2 promoter (U.S. Pat. Nos. 6,921,815 and 7,371,925; WO02/0078438); maize eep1 promoter (US Patent Application Publication Number 2007/0169226); maize end2 promoter (U.S. Pat. No. 6,528,704 and U.S. patent application Ser. No. 10/310,191); maize lec1 promoter (U.S. patent application Ser. No. 09/718,754); maize F3.7 promoter (Baszczynski, et al., (1997) *Maydica* 42:189-201); maize tb1 promoter (Hubbarda, et al., (2002) *Genetics* 162:1927-1935 and Wang, et al., (1999) *Nature* 398:236-239); maize eep2 promoter (U.S. patent application Ser. No. 10/817,483); maize thioredoxinH promoter (U.S. Provisional Patent Application Ser. No. 60/514,123); maize Zm40 promoter (U.S. Pat. No. 6,403,862 and WO 01/2178); maize mLIP15 promoter (U.S. Pat. No. 6,479,734); maize ESR promoter (U.S. patent application Ser. No. 10/786,679); maize PCNA2 promoter (U.S. patent application Ser. No. 10/388,359); maize cytokinin oxidase promoters (U.S. Pat. Nos. 6,921,815 and 7,371,925; WO02/0078438); promoters disclosed in Weigal, et al., (1992) *Cell* 69:843-859; Accession Number AJ131822; Accession Number Z71981; Accession Number AF049870 and shoot-preferred promoters disclosed in McAvoy, et al., (2003) *Acta Hort.* (ISHS) 625:379-385. Other dividing cell or meristematic tissue-preferred promoters that may be of interest have been disclosed in Ito, et al., (1994) *Plant Mol. Biol.* 24:863-878; Regad, et al., (1995) *Mo. Gen. Genet.* 248:703-711; Shaul, et al., (1996) *Proc. Natl. Acad. Sci* 93:4868-4872; Ito, et al., (1997) *Plant J.* 11:983-992 and Trehin, et al., (1997) *Plant Mol. Biol.* 35:667-672, all of which are hereby incorporated by reference herein. Other such promoters include the gamma zein, or glob 1 promoters disclosed in WO/2004/090143.

Inflorescence-preferred promoters include the promoter of chalcone synthase (Van der Meer, et al., (1990) *Plant Mol. Biol.* 15:95-109), LAT52 (Twell, et al., (1989) *Mol. Gen. Genet.* 217:240-245), pollen specific genes (Albani, et al., (1990) *Plant Mol. Biol.* 15:605), Zm13 (Buerrero, et al., (1993) *Mol. Gen. Genet.* 224:161-168), maize pollen-specific gene (Hamilton, et al., (1992) *Plant Mol. Biol.* 18:211-218), sunflower pollen expressed gene (Baltz, et al., (1992) *The Plant Journal* 2:713-721) and *B. napus* pollen specific genes (Arnoldo, et al., (1992) *J. Cell. Biochem*, Abstract Number Y101204).

Stress-inducible promoters include salt/water stress-inducible promoters such as P5CS (Zang, et al., (1997) *Plant Sciences* 129:81-89), cold-inducible promoters, such as, corl5a (Hajela, et al., (1990) *Plant Physiol.* 93:1246-1252), corl5b (Wlihelm, et al., (1993) *Plant Mol Biol* 23:1073-1077), wsc120 (Ouellet, et al., (1998) *FEBS Lett.* 423-324-328), ci7 (Kirch, et al., (1997) *Plant Mol. Biol.* 33:897-909), ci21A (Schneider, et al., (1997) *Plant Physiol.* 113:335-45), drought-inducible promoters, such as, Trg-31 (Chaudhary, et al., (1996) *Plant Mol. Biol.* 30:1247-57), osmotic inducible promoters, such as, Rab17 (Vilardell, et al., (1991) *Plant Mol. Biol.* 17:985-93) and osmotin (Raghothama, et al., (1993) *Plant Mol Biol* 23:1117-28) and heat inducible promoters, such as, heat shock proteins (Barros, et al. (1992) *Plant Mol.* 19:665-75; Marrs, et al., (1993) *Dev. Genet.* 14:27-41) and smHSP (Waters, et al., (1996) *J. Experimental Botany* 47:325-338). Other stress-inducible promoters include rip2 (U.S. Pat. No. 5,332,808 and US Patent Application Publication Number 2003/0217393) and rd29a (Yamaguchi-Shinozaki, et al., (1993) *Mol. Gen. Genetics* 236:331-340).

Stress-insensitive promoters can also be used in the methods of the invention. This class of promoters, as well as representative examples, are further described elsewhere herein.

Chemically-regulated promoters can be used to modulate the expression of a gene in a plant through the application of an exogenous chemical regulator. Depending upon the objective, the promoter may be a chemically-inducible promoter, where application of the chemical induces gene expression, or a chemical-repressible promoter, where application of the chemical represses gene expression. Chemically-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci USA* 88:10421-10425 and McNellis, et al., (1998) Plant J. 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156), herein incorporated by reference.

A promoter induced by cytokinin, such as the ZmCkx1-2 promoter (U.S. Pat. Nos. 6,921,815 and 7,371,925), may also be used in the methods and compositions of the invention. Such a construct would amplify biosynthesis of cytokinin occurring in developmental stages and/or tissues of interest. Other cytokinin-inducible promoters are described in pending U.S. patent application Ser. Nos. 12/165,935 and 12/464,527, all hereby incorporated by reference.

Additional inducible promoters include heat shock promoters, such as Gmhsp17.5-E (soybean) (Czarnecka, et al., (1989) *Mol Cell Biol.* 9(8):3457-3463), APX1 gene promoter (Arabidopsis) (Storozhenko, et al., (1998) *Plant Physiol.* 118 (3):1005-1014), Ha hsp17.7 G4 (*Helianthus annuus*) (Almoguera, et al., (2002) *Plant Physiol.* 129(1):333-341) and Maize Hsp70 (Rochester, et al., (1986) *EMBO J.* 5: 451-8).

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotides or polypeptides into plants are known in the art and include, but are not limited to, stable transformation methods, transient transformation methods and virus-mediated methods.

"Stable transformation" is intended to mean that the nucleotide construct of interest introduced into a plant integrates into the genome of the plant and is capable of being inherited by the progeny thereof. "Transient transformation" is intended to mean that a sequence is introduced into the plant and is only temporarily expressed or present in the plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips (Springer-Verlag, Berlin); McCabe, et al., (1988) *Biotechnology* 6:923-926) and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Hogue, et al., (2005) *Plant Cell Tissue & Organ Culture* 82(1):45-55 (rice); Sreekala, et al., (2005) *Plant Cell Reports* 24(2):86-94 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*), all of which are herein incorporated by reference.

In specific embodiments, the kn1 sequences of the invention can be provided to a plant using a variety of transient transformation methods. Such transient transformation methods include, but are not limited to, the introduction of the kn1 protein or variants and fragments thereof directly into the plant or the introduction of a kn1 transcript into the plant. Such methods include, for example, microinjection or particle bombardment. See, for example, Crossway, et al., (1986) *Mol. Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784, all of which are herein incorporated by reference. Alternatively, the kn1 polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethyenlimine (PEI; Sigma #P3143).

In other embodiments, the knotted1 encoding polynucleotide may be introduced into plants by contacting plants with a virus or viral nucleic acids. Generally, such methods involve incorporating a nucleotide construct of the invention within a viral DNA or RNA molecule. It is recognized that a kn1 polynucleotide of the invention may be initially synthesized as part of a viral polyprotein, which later may be processed by proteolysis in vivo or in vitro to produce the desired recombinant protein. Further, it is recognized that promoters useful for the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889, 190, 5,866,785, 5,589,367, 5,316,931 and Porta, et al., (1996) *Molecular Biotechnology* 5:209-221, herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO 99/25821, WO 99/25854, WO 99/25840, WO 99/25855 and WO 99/25853, and U.S. Pat. Nos. 6,187,994; 6,552,248; 6,624,297; 6,331,661; 6,262,341; 6,541,231; 6,664,108; 6,300,545; 6,528,700 and 6,911,575, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84. These plants may then be grown and pollinated with either the same transformed strain or different strains and the resulting progeny having expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

Pedigree breeding starts with the crossing of two genotypes, such as an elite line of interest and one other line having one or more desirable characteristics (e.g., having stably incorporated a polynucleotide of the invention, having a modulated activity and/or level of the polypeptide of the invention, etc.) which complements the elite line of interest. If the two original parents do not provide all the desired characteristics, other sources can be included in the breeding population. In the pedigree method, superior plants are self-fertilized (selfing) and selected in successive filial generations. In the succeeding filial generations the heterozygous condition gives way to homogeneous lines as a result of self-pollination and selection. Typically in the pedigree method of breeding, five or more successive filial generations of selfing and selection are practiced: F1→F2; F2→F3; F3→F4; F4→F5, etc. After a sufficient amount of inbreeding, successive filial generations will serve to increase seed of the developed inbred. In specific embodiments, the F5 inbred line comprises homozygous alleles at about 95% or more of its loci.

The backcross breeding method is a technique used to transfer one or more specifically desirable traits from one line, the donor parent, to an inbred line called the recurrent parent, which has overall good agronomic characteristics yet lacks that desirable trait or traits. In addition to being used to create a backcross conversion hybrid, backcrossing can also be used in combination with pedigree breeding to modify an elite line of interest and create a segregating population of breeding lines. The backcross and pedigree breeding procedures can be used to move the progeny toward the genotype of the recurrent parent but at the same time retain many components of the non-recurrent parent by stopping the backcrossing at an early stage and proceeding with selfing and selection. For example, a donor line is created. This donor line may be crossed to a recurrent parent (an elite line or hybrid) to create filial one (F1) progeny seed. The F1 seed can then be backcrossed to the recurrent parental line to create a backcross) (BC1) F1 population. The BC1F1 plant can be backcrossed to the recurrent parent to create a BC2F1. Additional backcross cycles allow for additional recovery of the recurrent parent genotype. On average, the BC1 will be 75% recurrent parent the BC2 will be 87.5% recurrent parent, the BC3 will be 93.75% recurrent parent, the BC4 will be 96.88% recurrent parent and the BC5 will be 98.44% recurrent parent. The BC progeny can be selfed at any point after a backcross cycle and selected so that the new developed inbred lines have many of the attributes of the recurrent parent and possess the desired trait or traits of the non-recurrent parent. This approach leverages the value and strengths of the recurrent parent and induces a desired trait or traits for use in new hybrids and variety development breeding.

Therefore, an embodiment of this invention is a method of making a backcross conversion of a line of interest, comprising the steps of crossing into an elite recurrent line of interest a donor plant comprising a mutant gene or transgene conferring a desired trait (i.e., a plant with a kn1 polypeptide or a plant with modulation in the level of cytokinin (an increase or a decrease) or any plant phenotype resulting from the mutation or transgene (such plant phenotypes are discussed elsewhere herein), selecting an F1 progeny plant comprising the mutant gene or transgene conferring the desired trait and backcrossing the selected F1 progeny plant to a plant of the recurrent line of interest. This method may further comprise the step of obtaining a molecular marker profile of the recurrent line of interest and using the molecular marker profile to select for a progeny plant with the desired trait and the molecular marker profile of the recurrent line of interest. In the same manner, this method may be used to produce F1 hybrid seed by adding a final step of crossing the desired trait conversion of the inbred line of interest with a different plant to make F1 hybrid seed comprising a mutant gene or transgene conferring the desired trait. For variental development, the F1 seed is selfed for subsequent filial generations and plants are selected using recurrent or mass selection techniques to develop finished lines with the trait of interest and desired phenotypic characteristics.

Recurrent selection is a method used in a plant breeding program to improve a population of plants. The method entails individual plants cross pollinating with each other to form progeny (in the case of maize) or allowing a population to self-pollinate to form progeny (in the case of soybean). The progeny are grown and the superior progeny selected by any number of selection methods, which include individual plant, half-sib progeny, full-sib progeny, selfed progeny and topcrossing. The selected progeny are cross-pollinated with each other (in the case of maize) or allowed to self-pollinate (in the case of soybean) to form progeny for another population. This population is planted and again superior plants are selected to cross pollinate with each other (in the case of maize) or self-pollinate (in the case of soybean). Recurrent selection is a cyclical process and therefore can be repeated as many times as desired. The objective of recurrent selection is to improve the traits of a population. The improved population can then be used as a source of breeding material to obtain inbred lines to be used in hybrids, as inbred lines for varietal development, or as parents for a synthetic cultivar. A synthetic cultivar is the resultant progeny formed by the intercrossing of several selected inbreds.

Mass selection is a useful technique especially when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14) or ultraviolet radiation (preferably from 2500 to 2900 nm) or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid or acridines. Once a desired trait is observed through mutagenesis the trait may then be incorporated into existing germplasm by traditional breeding techniques, such as backcrossing. Details of mutation breeding can be found in "Principles of Cultivar Development," Fehr, 1993 Macmillan Publishing Company, the disclosure of which is incorporated herein by reference. In addition, mutations created in other lines may be used to produce a backcross conversion of elite lines that comprises such mutations.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*) and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (Tu/ipa spp.), daffodils (*Narcissus* spp.), petunias (*Petunia hybrida*), carnation (*Dianthus caryophyllus*), poinsettia (*Euphorbia pulcherrima*) and chrysanthemum.

Conifers that may be employed in practicing the present invention include, for example, pines such as loblolly pine (*Pinus taeda*), slash pine (Pinus elliotil), ponderosa pine (*Pinus ponderosa*), lodgepole pine (*Pinus contorta*) and Monterey pine (*Pinus radiata*), Douglas-fir (*Pseudotsuga menziesii*), Western hemlock (*Tsuga canadensis*), Sitka spruce (*Picea glauca*), redwood (*Sequoia sempervirens*), true firs such as silver fir (*Abies amabilis*) and balsam fir (*Abies balsamea*) and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal and in yet other embodiments corn plants are optimal.

Other plants of interest include grain plants that provide seeds of interest, oil-seed plants and leguminous plants. Seeds of interest include grain seeds, such as maize, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of this invention to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (*penicillinase*) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E coli*. is also useful. Examples of such markers include genes specifying resistance to ampicillin, tetracycline or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-235); Mosbach, et al., (1983) *Nature* 302:543-545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous polynucleotides in yeast is well known (Sherman, et al., (1982) *Methods in Yeast Genetics*, Cold Spring Harbor Laboratory). Two widely utilized yeasts for production of eukaryotic proteins are *Saccharomyces cer-* evisiae and *Pichia pastoris*. Vectors, strains and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase and an origin of replication, termination sequences and the like as desired. A protein of the present invention, once expressed, can be isolated from yeast by lysing the cells and applying standard protein isolation techniques to the lists. The monitoring of the purification process can be accomplished by using Western blot techniques or radioimmunoassay or other standard immunoassay techniques.

The sequences of the present invention can also be ligated to various expression vectors for use in transfecting cell cultures of, for instance, mammalian, insect or plant origin. Illustrative cell cultures useful for the production of the peptides are mammalian cells. A number of suitable host cell lines capable of expressing intact proteins have been developed in the art and include the HEK293, BHK21 and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49) and necessary processing information sites, such as ribosome binding sites, RNA splice sites, polyadenylation sites (e.g., an SV40 large T Ag poly A addition site) and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider, (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., (1983) *J. Virol.* 45:773-781). Additionally, gene sequences to control replication in the host cell may be incorporated into the vector such as those found in bovine papilloma virus type-vectors (Saveria-Campo, (1985) *DNA Cloning Vol. II a Practical Approach*, Glover, Ed., IRL Press, Arlington, Va., pp. 213-238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics and micro-injection of the DNA directly into the cells. The transfected cells are cultured by means well known in the art (Kuchler, (1997) *Biochemical Methods in Cell Culture and Virology*, Dowden, Hutchinson and Ross, Inc.).

II. Modulating the Concentration and/or Activity of a knotted 1 Polypeptide

A method for modulating the concentration and/or activity of the kn1 polypeptide of the present invention in a plant is provided. In general, concentration and/or activity of the kn1 polypeptide is increased or reduced by at least 1%, 5%, 10%, 20%, 30%, 40%, 50%, 60% 70%, 80% or 90% or more, relative to a native control plant, plant part or cell which does not comprise the introduced sequence. Modulation of the concentration and/or activity may occur at one or more stages of development. In specific embodiments, the polypeptides of the present invention are modulated in monocots, such as maize, or in dicots, such as soybean.

The expression level of the kn1 polypeptide may be measured directly, for example, by assaying for the level of the kn1 polypeptide in the plant. Alternatively, the effect of modulated expression of the kn1 polypeptide may be measured indirectly, for example, by measuring the cytokinin synthesis activity in the plant. See, for example, FIG. 5. Methods for assaying for cytokinin synthesis activity are described elsewhere herein.

In specific embodiments, the polypeptide or the polynucleotide of the invention is introduced into the plant cell. Subsequently, a plant cell having the introduced sequence of the invention is selected using methods known to those of skill in the art such as, but not limited to, Southern blot analysis, DNA sequencing, PCR analysis or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

It is also recognized that the level and/or activity of the polypeptide may be modulated by employing a polynucleotide that is not capable of directing, in a transformed plant, the expression of a protein or RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides and recombinogenic oligonucleobases. Such nucleotide constructs and methods of use are known in the art. See, U.S. Pat. Nos. 5,565,350, 5,731,181, 5,756,325, 5,760,012, 5,795,972 and 5,871,984, all of which are herein incorporated by reference. See also, WO 98/49350, WO 99/07865, WO 99/25821 and Beetham, et al., (1999) *Proc. Natl. Acad. Sci. USA* 96:8774-8778, herein incorporated by reference.

It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of a polynucleotide into a cell. For example, the polynucleotide, or any part thereof, may incorporate into the genome of the plant. Alterations to the genome include, but are not limited to, additions, deletions and substitutions of nucleotides into the genome. While the methods of the present invention do not depend on additions, deletions and substitutions of any particular number of nucleotides, it is recognized that such additions, deletions or substitutions comprise at least one nucleotide.

It is further recognized that modulating the level and/or activity of the kn1 sequence can be performed to elicit the effects of the sequence only during certain developmental stages and to switch the effect off in other stages where expression is not desirable. Control of kn1 expression can be obtained via use of inducible or tissue-preferred promoters. Alternatively, the gene could be inverted or deleted using site-specific recombinases, transposons or recombination systems, which would also regulate expression of the kn1 sequence.

A "subject plant or plant cell" is one in which genetic alteration, such as transformation, has been effected as to a gene of interest or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest or (e) the subject plant or plant cell itself, under conditions in which the gene of interest is not expressed.

In the present case, for example, changes in cytokinin levels, including changes in absolute amounts of cytokinin, cytokinin ratios, cytokinin activity or cytokinin distribution, or changes in plant or plant cell phenotype, such as altered flowering time, seed set, branching, senescence, stress tolerance or root mass could be measured by comparing a subject plant or plant cell to a control plant or plant cell.

In certain embodiments the nucleic acid constructs of the present invention can be used in combination ("stacked") with other polynucleotide sequences of interest in order to create plants with a desired phenotype. The polynucleotides of the present invention may be stacked with any gene or combination of genes and the combinations generated can include multiple copies of any one or more of the polynucleotides of interest. The desired combination may affect one or more traits; that is, certain combinations may be created for modulation of gene expression affecting cytokinin activity. For example, up-regulation of cytokinin synthesis may be combined with down-regulation of cytokinin degradation. Other combinations may be designed to produce plants with a variety of desired traits, such as those previously described.

A. Increasing the Activity and/or Concentration of a kn1 Polypeptide

Methods are provided to increase the activity and/or concentration of the kn1 polypeptide of the invention. An increase in the concentration and/or activity of the kn1 polypeptide of the invention can be achieved by integrating into the plant a kn1 polynucleotide. As discussed elsewhere herein, many methods are known in the art for integrating a polynucleotide to a plant including, but not limited to, direct introduction of the polynucleotide into the plant and introducing into the plant (transiently or stably) a polynucleotide construct encoding a polypeptide that induces cytokinin synthesis activity. It is also recognized that the methods of the invention may employ a polynucleotide that is not capable of directing, in the transformed plant, the expression of a protein or RNA. Thus, the level and/or activity of a kn1 polypeptide may be increased by altering the gene encoding the kn1 polypeptide or its promoter. See, e.g., Kmiec, U.S. Pat. No. 5,565,350; Zarling, et al., PCT/US93/03868. Therefore mutagenized plants that carry mutations in kn1 genes, where the mutations increase expression of the kn1 gene or increase the cytokinin synthesis activity of the encoded kn1 polypeptide, are provided. As described elsewhere herein, methods to assay for an increase in protein concentration or an increase in cytokinin synthesis activity are known.

B. Reducing the Activity and/or Concentration of a kn1 Polypeptide

Methods are provided to reduce or eliminate the activity and/or concentration of the kn1 polypeptide by transforming a plant cell with an expression cassette that expresses a polynucleotide that inhibits the expression of the kn1 polypeptide. The polynucleotide may inhibit the expression of a kn1 polypeptide directly, by preventing translation of the kn1 polypeptide messenger RNA, or indirectly, by encoding a molecule that inhibits the transcription or translation of a kn1 polypeptide gene encoding a kn1 polypeptide. Methods for inhibiting or eliminating the expression of a gene in a plant are well known in the art and any such method may be used in the present invention to inhibit the synthesis of kn1 polypeptides.

In accordance with the present invention, the expression of a kn1 polypeptide is inhibited if the level of the kn1 polypeptide is statistically lower than the level of the same kn1 polypeptide in a plant that has not been genetically modified or mutagenized to inhibit the expression of that kn1 polypeptide. In particular embodiments of the invention, the protein level of the kn1 polypeptide in a modified plant according to the invention is less than 99%, less than 95%, less than 90%, less than 80%, less than 70%, less than 60%, less than 50%, less than 40%, less than 30%, less than 20%, less than 10% or less than 5% of the protein level of the same kn1 polypeptide in a plant that is not a mutant or that has not been genetically modified to inhibit the synthesis of that kn1 polypeptide. The expression level of the kn1 polypeptide may be measured directly, for example, by assaying for the level of the kn1 polypeptide accumulated in the cell or plant, or indirectly, for example, by measuring cytokinin levels in the cell or plant. Methods for determining cytokinin synthesis activity of the kn1 polypeptide are described elsewhere herein.

In other embodiments of the invention, the activity of one or more kn1 polypeptides is reduced or eliminated by transforming a plant cell with an expression cassette comprising a polynucleotide encoding a polypeptide that inhibits the activity of one or more kn1 polypeptides. The activity of a kn1 polypeptide is inhibited according to the present invention if the cytokinin synthesis activity of the kn1 polypeptide is statistically lower than the cytokinin synthesis activity of the same kn1 polypeptide in a plant that has not been genetically modified to inhibit the cytokinin synthesis activity of that kn1 polypeptide. In particular embodiments of the invention, the cytokinin synthesis activity of the kn1 polypeptide in a modified plant according to the invention is less than 99%, less than 95%, less than 90%, less than 80%, less than 70%, less than 60%, less than 50%, less than 40%, less than 30%, less than 20%, less than 10% or less than 5% of the cytokinin synthesis activity of the same kn1 polypeptide in a plant that that has not been genetically modified to inhibit the expression of that kn1 polypeptide. The cytokinin synthesis activity of a kn1 polypeptide is "eliminated" according to the invention when it is not detectable by the assay methods described elsewhere herein. Methods of determining the cytokinin synthesis activity of a kn1 polypeptide are described elsewhere herein.

In other embodiments, the activity of a kn1 polypeptide may be reduced or eliminated by disrupting the gene encoding the kn1 polypeptide. The invention encompasses mutagenized plants that carry mutations in kn1 genes, where the mutations reduce expression of the kn1 gene or inhibit the cytokinin synthesis activity of the encoded kn1 polypeptide.

Thus, many methods may be used to reduce or eliminate the activity of a kn1 polypeptide. More than one method may be used to reduce the activity of a single kn1 polypeptide. In addition, combinations of methods may be employed to reduce or eliminate the activity of two or more different kn1 polypeptides.

Non-limiting examples of methods of reducing or eliminating the expression of a kn1 polypeptide are given below.

1. Polynucleotide-Based Methods

In some embodiments of the present invention, a plant cell is transformed with an expression cassette that is capable of expressing a polynucleotide that inhibits the expression of a kn1 sequence. The term "expression" as used herein refers to the biosynthesis of a gene product, including the transcription and/or translation of said gene product. For example, for the purposes of the present invention, an expression cassette capable of expressing a polynucleotide that inhibits the expression of at least one kn1 sequence is an expression cassette capable of producing an RNA molecule that inhibits the transcription and/or translation of at least one kn1 polypeptide. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a kn1 sequence are given below.

i. Sense Suppression/Cosuppression

In some embodiments of the invention, inhibition of the expression of a kn1 polypeptide may be obtained by sense suppression or cosuppression. For cosuppression, an expression cassette is designed to express an RNA molecule corresponding to all or part of a messenger RNA encoding a kn1 polypeptide in the "sense" orientation. Over expression of the RNA molecule can result in reduced expression of the native gene. Accordingly, multiple plant lines transformed with the cosuppression expression cassette are screened to identify those that show the greatest inhibition of kn1 polypeptide expression.

The polynucleotide used for cosuppression may correspond to all or part of the sequence encoding the kn1 polypeptide, all or part of the 5' and/or 3' untranslated region of a kn1 polypeptide transcript or all or part of both the coding sequence and the untranslated regions of a transcript encoding a kn1 polypeptide. In some embodiments where the polynucleotide comprises all or part of the coding region for the kn1 polypeptide, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin, et al., (2002) Plant Cell 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) Proc. Natl. Acad. Sci USA 91:3490-3496; Jorgensen, et al., (1996) Plant Mol. Biol. 31:957-973; Johansen and Carrington, (2001) Plant Physiol. 126:930-938; Broin, et al., (2002) Plant Cell 14:1417-1432; Stoutjesdijk, et al., (2002) Plant Physiol. 129:1723-1731; Yu, et al., (2003) Phytochemistry 63:753-763 and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference.

ii. Antisense Suppression

In some embodiments of the invention, inhibition of the expression of the kn1 polypeptide may be obtained by antisense suppression. For antisense suppression, the expression cassette is designed to express a RNA molecule complementary to all or part of a messenger RNA encoding the kn1 polypeptide. Over expression of the antisense RNA molecule can result in reduced expression of the native gene. Accordingly, multiple plant lines transformed with the antisense suppression expression cassette are screened to identify those that show the greatest inhibition of kn1 polypeptide expression.

The polynucleotide for use in antisense suppression may correspond to all or part of the complement of the sequence encoding the kn1 polypeptide, all or part of the complement of the 5' and/or 3' untranslated region of the kn1 polypeptide transcript or all or part of the complement of both the coding sequence and the untranslated regions of a transcript encoding the kn1 polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) Plant Physiol. 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the invention, inhibition of the expression of a kn1 polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of kn1 polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743 and WO 99/49029, WO 99/53050, WO 99/61631 and WO 00/49035, each of which is herein incorporated by reference.

iv. Hairpin RNA Interference and Intron-Containing Hairpin RNA Interference

In some embodiments of the invention, inhibition of the expression of one or more kn1 polypeptides may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes and the RNA interference they induce is inherited by subsequent generations of plants. See, for example, Chuang and Meyerowitz, (2000) *Proc. Natl. Acad. Sci USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini, et al., *BMC Biotechnology* 3:7 and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

Alternatively, the base-paired stem region may correspond to a portion of a promoter sequence controlling expression of the gene to be inhibited. Transcriptional gene silencing (TGS) may be accomplished through use of hpRNA constructs wherein the inverted repeat of the hairpin shares sequence identity with the promoter region driving expression of a gene to be silenced. See, for example, U.S. patent application Ser. No. 11/014,071, filed 16 Dec. 2004. Processing of the hpRNA into short RNAs which can interact with the homologous promoter region may trigger degradation or methylation to result in silencing (Aufsatz, et al., (2002) *PNAS* 99(4):16499-16506; Mette, et al., (2000) *EMBO J.* 19(19):5194-5201).

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407: 319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for a kn1 polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of a kn1 polypeptide. Thus, the polynucleotide causes the degradation of the endogenous messenger RNA, resulting in reduced expression of the kn1 polypeptide. This method is described, for example, in U.S. Pat. No. 4,987,071, herein incorporated by reference.

vii. Small Interfering RNA or Micro RNA

In some embodiments of the invention, inhibition of the expression of one or more kn1 polypeptides may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of kn1 polypeptide expression, the 22-nucleotide sequence is selected from a kn1 polypeptide transcript sequence and contains 22 nucleotides encoding said kn1 polypeptide sequence in sense orientation and 21 nucleotides of a corresponding antisense sequence that is complementary to the sense sequence. miRNA molecules are highly efficient at inhibiting the expression of endogenous genes and the RNA interference they induce is inherited by subsequent generations of plants.

2. Polypeptide-Based Inhibition of Gene Expression

In one embodiment, the polynucleotide encodes a zinc finger protein that binds to a gene encoding a kn1 polypeptide, resulting in reduced expression of the gene. In particular embodiments, the zinc finger protein binds to a regulatory region of a kn1 polypeptide gene. In other embodiments, the zinc finger protein binds to a messenger RNA encoding a kn1 polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Application Publication Number 2003/0037355, each of which is herein incorporated by reference.

3. Polypeptide-Based Inhibition of Protein Activity

In some embodiments of the invention, the polynucleotide encodes an antibody that binds to at least one kn1 polypeptide and reduces the cytokinin synthesis activity of the kn1 polypeptide. In another embodiment, the binding of the antibody results in increased turnover of the antibody-kn1 polypeptide complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of a kn1 polypeptide is reduced or eliminated by disrupting the gene encoding the kn1 polypeptide. The gene encoding the kn1 polypeptide may be disrupted by any method known in the art. For example, in one embodiment, the gene is disrupted by transposon tagging. In another embodiment, the gene is disrupted by mutagenizing plants using random or targeted mutagenesis and selecting for plants that have reduced kn1 activity. In some embodiments, presence of an overlapping open reading frame (oORF) may impact transcription and/or translation of a heterologous gene, thereby modulating its expression level.

i. Transposon Tagging

In one embodiment of the invention, transposon tagging is used to reduce or eliminate the cytokinin synthesis activity of one or more kn1 polypeptides. Transposon tagging comprises inserting a transposon within an endogenous kn1 gene to reduce or eliminate expression of the kn1 polypeptide. "kn1 gene" is intended to mean the gene that encodes a kn1 polypeptide according to the invention.

In this embodiment, the expression of one or more kn1 polypeptides is reduced or eliminated by inserting a transposon within a regulatory region or coding region of the gene encoding the kn1 polypeptide. A transposon that is within an exon, intron, 5' or 3' untranslated sequence, a promoter or any other regulatory sequence of a kn1 polypeptide gene may be used to reduce or eliminate the expression and/or activity of the encoded kn1 polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928. In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764, each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis and fast neutron deletion mutagenesis used in a reverse genetics sense (with PCR) to identify plant lines in which the endogenous gene has been deleted. For examples of these methods see Ohshima, et al., (1998) *Virology* 243:472-481; Okubara, et al., (1994) *Genetics* 137:867-874 and Quesada, et al., (2000) *Genetics* 154:421-436, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (kn1 activity) of the encoded protein are well known in the art. Insertional mutations in gene exons usually result in null-mutants. Mutations in conserved residues are particularly effective in inhibiting the cytokinin synthesis activity of the encoded protein. Conserved residues of plant kn1 polypeptides suitable for mutagenesis with the goal to eliminate kn1 activity have been described. See, for example, FIG. 1. Such mutants can be isolated according to well-known procedures and mutations in different kn1 loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more kn1 polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleobases. Such vectors and methods of use are known in the art. See, for example, U.S. Pat. Nos. 5,565,350; 5,731,181; 5,756,325; 5,760,012; 5,795,972 and 5,871,984, each of which are herein incorporated by reference. See also, WO 98/49350, WO 99/07865, WO 99/25821 and Beetham, et al., (1999) *Proc. Natl. Acad. Sci. USA* 96:8774-8778, each of which is herein incorporated by reference.

III. Modulating Cytokinin Level and/or Activity

As used herein, "cytokinin" refers to a class or member of the class, of plant-specific hormones that play a central role during the cell cycle and influence numerous developmental programs. Cytokinins comprise an $N^6$-substituted purine derivative. Representative cytokinins include isopentenyladenine ($N^6$-($\Delta^2$-isopentenyl)adenine (hereinafter, iP), zeatin (6-(4-hydroxy-3-methylbut-trans-2-enylamino) purine) (hereinafter, Z) and dihydrozeatin (DZ). The free bases and their ribosides (iPR, ZR and DZR) are believed to be the active compounds. Additional cytokinins are known. See, for example, U.S. Pat. No. 5,211,738 and Keiber, et al., (2002) *Cytokinins, The Arabidopsis Book*, American Society of Plant Biologists, both of which are herein incorporated by reference.

"Modulating the cytokinin level" includes any statistically significant decrease or increase in cytokinin level and/or activity in the plant when compared to a control plant. For example, modulating the level and/or activity can comprise either an increase or a decrease in overall cytokinin content of about 0.1%, 0.5%, 1%, 3% 5%, 10%, 15%, 20%, 25%, 30%, 35%, 40%, 45%, 50%, 55%, 60%, 65%, 70%, 75%, 80%, 85%, 90%, 95% or greater when compared to a control plant or plant part. Alternatively, the modulated level and/or activity of the cytokinin can include about a 0.2 fold, 0.5 fold, 2 fold, 4 fold, 8 fold, 16 fold, 32 fold or greater overall increase or decrease in cytokinin level/activity in the plant or a plant part when compared to a control plant or plant part.

It is further recognized that the modulation of the cytokinin level/activity need not be an overall increase/decrease in cytokinin level and/or activity, but also includes a change in tissue distribution of the cytokinin. Moreover, the modulation of the cytokinin level/activity need not be an overall increase/decrease in cytokinins, but also includes a change in the ratio of various cytokinin derivatives. For example, the ratio of various cytokinin derivatives such as isopentenyladenine-type, zeatin-type or dihydrozeatin-type cytokinins, and the like, could be altered and thereby modulate the level/activity of the cytokinin of the plant or plant part when compared to a control plant.

Methods for assaying a modulation in cytokinin level and/or activity are known in the art. For example, representative methods for cytokinin extraction, immunopurification, HPLC separation, and quantification by ELISA methods can be found, for example, in Faiss, et al., (1997) *Plant J.* 12:401-415. See also, Werner, et al., (2001) *PNAS* 98:10487-10492) and Dewitte, et al., (1999) *Plant Physiol.* 119:111-121. Each of these references is herein incorporated by reference. As discussed elsewhere herein, modulation in cytokinin level and/or activity can further be detected by monitoring for particular plant phenotypes. Such phenotypes are described elsewhere herein.

In specific methods, the level and/or activity of a cytokinin in a plant is increased by increasing the level or activity of the kn1 polypeptide in the plant. Methods for increasing the level and/or activity of kn1 polypeptides in a plant are discussed elsewhere herein. Briefly, such methods comprise providing a kn1 polypeptide of the invention to a plant and thereby increasing the level and/or activity of the kn1 polypeptide. In other embodiments, a kn1 nucleotide sequence encoding a kn1 polypeptide can be provided by introducing into the plant a polynucleotide comprising a kn1 nucleotide sequence of the invention, expressing the kn1 sequence and thereby increasing the level and/or activity of a cytokinin or other gene products in the plant or plant part when compared to a control plant. In some embodiments, the kn1 nucleotide construct introduced into the plant is stably incorporated into the genome of the plant.

In other methods, the level and/or activity of cytokinin or other gene products in a plant is decreased by decreasing the level and/or activity of one or more of the kn1 polypeptides in the plant. Such methods are disclosed in detail elsewhere herein. In one such method, a kn1 nucleotide sequence is introduced into the plant and expression of the kn1 nucleotide sequence decreases the activity of the kn1 polypeptide and thereby decreases the level and/or activity of a cytokinin in the plant or plant part when compared to a control plant or plant part. In other embodiments, the kn1 nucleotide construct introduced into the plant is stably incorporated into the genome of the plant.

As discussed above, one of skill will recognize the appropriate promoter to use to modulate the level/activity of a cytokinin in the plant. Exemplary promoters for this embodiment have been disclosed elsewhere herein.

Accordingly, the present invention further provides plants having a modulated level/activity of a cytokinin or other gene products when compared to the cytokinin level/activity of a control plant. In one embodiment, the plant of the invention has an increased level/activity of the kn1 polypeptide of the invention and thus has an increased level/activity of cytokinin or other gene products. In other embodiments, the plant of the invention has a reduced or eliminated level of the kn1 polypeptide of the invention and thus has a decreased level/activity of a cytokinin. In certain embodiments, such plants have stably incorporated into their genome a nucleic acid molecule comprising a kn1 nucleotide sequence of the invention operably linked to a promoter that drives expression in the plant cell.

Methods for establishing callus from explants are known. For example, roots, stems, buds and aseptically germinated seedlings are just a few of the sources of tissue that can be used to induce callus formation. Generally, young and actively growing tissues (i.e., young leaves, roots, meristems or other tissues) are used, but are not required. Callus formation is controlled by growth regulating substances present in the medium (auxins and cytokinins). The specific concentrations of plant regulators needed to induce callus formation vary from species to species and can even depend on the source of explant. In some instances, it is advised to use different growth substances (e.g., 2,4-D or NAA) or a combination of them during tests, since some species may not respond to a specific growth regulator. In addition, culture conditions (i.e., light, temperature, etc.) can also influence the establishment of callus. Once established, callus cultures can be used to initiate shoot regeneration. See, for example, Gurel, et al., (2001) *Turk J. Bot.* 25:25-33; Dodds, et al., (1995) Experiments in Plant Tissue Culture, Cambridge University Press; Gamborg, (1995) *Plant Cell, Tissue and Organ Culture*, eds. Phillips and US Patent Application Publication Number 2003/0180952, all of which are herein incorporated by reference.

It is further recognized that increasing seed size and/or weight can be accompanied by an increase in the rate of growth of seedlings or an increase in vigor. In addition, modulating the plant's tolerance to stress, as discussed elsewhere herein, along with modulation of root, shoot and leaf development, can increase plant yield and vigor. As used herein, the term "vigor" refers to the relative health, productivity and rate of growth of the plant and/or of certain plant parts and may be reflected in various developmental attributes, including, but not limited to, concentration of chlorophyll, photosynthetic rate, total biomass, root biomass, grain quality and/or grain yield. Vigor may relate to the ability of a plant to grow rapidly during early development and to the successful establishment, after germination, of a well-developed root system and a well-developed photosynthetic apparatus. Vigor may be determined with reference to different genotypes under similar environmental conditions or with reference to the same or different genotypes under different environmental conditions.

Accordingly, the present invention further provides plants having modulated shoot and/or leaf development when compared to a control plant. In some embodiments, the plant of the invention has an increased level/activity of the kn1 polypeptide of the invention. In other embodiments, the plant of the invention has a decreased level/activity of the kn1 polypeptide of the invention.

IV. Modulating Reproductive Tissue Development

Abortion of flowers and pods is a common occurrence in soybeans and is believed to limit yield (Abernethy, et al., (1997) *Can J Plant Sci* 57:713-716; Dybing, et al., (1986) *Plant Physiol* 81:1069-1074). Cytokinins have been shown to play an important role during flower and pod development. Exogenous application of benzyladenine (a cytokinin) to the raceme decreases abortion of flowers and/or pods (Dyer, et al., (1988) In: Pharis and Rood, eds. Plant growth substances. New York: Springer-Verlag, 457-467; Peterson, et al., (1990) *Botanical Gazette* 151:322-330; Mosjidis, et al., (1993) Annals of Botany 71:193-199; Reese, et al., (1995) *J Exptl Botany* 46(289):957-964) and a strong body of evidence supports a role for cytokinins in the regulation of flowering and seed setting in soybean (Huff and Dybing, (1980) *J Exptl Botany* 31:51-762; Ghiasi, et al., (1987) *Plant Physiol* 81:1069-1074; Peterson, et al., (1990) *Botanical Gazette* 151: 322-330; Wiebold, (1990) *Agron J* 82:85-88; Mosjidis, et al., (1993), supra; Reese, et al., (1995), supra; Nagel, et al., (2001) *Annals of Botany* 88:27-31). An increase in the number of pods and seeds in response to cytokinin treatments supports the hypothesis that increasing cytokinin concentration in developing flowers and pods using appropriate promoters would result in increased total seed production by soybean plants.

Methods for modulating reproductive tissue development are provided. In one embodiment, methods are provided to modulate floral development in a plant. By "modulating floral development" is intended any alteration in a structure of a plant's reproductive tissue as compared to a control plant or plant part. "Modulating floral development" further includes any alteration in the timing of the development of a plant's reproductive tissue (i.e., delayed or accelerated floral development) when compared to a control plant or plant part. Macroscopic alterations may include changes in size, shape, number or location of reproductive organs, the developmental time period during which these structures form or the ability to maintain or proceed through the flowering process in times of environmental stress. Microscopic alterations may include changes to the types or shapes of cells that make up the reproductive organs.

The method for modulating floral development in a plant comprises modulating (either increasing or decreasing) the level and/or activity of the kn1 polypeptide in a plant. In one method, a kn1 sequence of the invention is provided. A kn1 nucleotide sequence can be provided by introducing into the plant a polynucleotide comprising a kn1 nucleotide sequence of the invention, expressing the kn1 sequence and thereby modifying floral development. In some embodiments, the kn1 nucleotide construct introduced into the plant is stably incorporated into the genome of the plant.

As discussed above, one of skill will recognize the appropriate promoter to use to modulate floral development in the plant. Exemplary promoters for this embodiment include inducible promoters, shoot-preferred promoters, inflorescence-preferred promoters (including developing-female-inflorescence-preferred promoters), seed-preferred promoters and pod-preferred promoters, including those listed elsewhere herein.

In specific methods, floral development is modulated by increasing the level and/or activity of the kn1 sequence of the invention. Such methods can comprise introducing a kn1 nucleotide sequence into the plant and increasing the activity of the kn1 polypeptide. In some methods, the kn1 nucleotide construct introduced into the plant is stably incorporated into the genome of the plant. An increase in the level and/or activity of the kn1 sequences can result in one or more alterations in floral development including, but not limited to, accelerated flowering, increased number of flowers, increasing the rate of floral retention, increasing the rate of pod retention and improved seed set when compared to a control plant. In addition, an increase in the level or activity of the kn1 sequences can result in the prevention of flower and/or pod senescence and an alteration in embryo number per pod. See, Young, et al., (2004) *Plant J.* 38:910-22. Methods for measuring such developmental alterations in floral development are known in the art. See, for example, Mouradov, et al., (2002) *The Plant Cell* S111-S130, herein incorporated by reference.

In other methods, floral development is modulated by decreasing the level and/or activity of the kn1 sequence of the invention. A decrease in the level and/or activity of the kn1 sequence can result in kernel abortion and infertile female inflorescence. Inducing delayed flowering or inhibiting flowering which can be used to enhance yield in forage crops such as alfalfa.

Accordingly, the present invention further provides plants having modulated floral development when compared to the floral development of a control plant. Compositions include plants having a decreased level/activity of the kn1 polypeptide of the invention and having an altered floral development. Compositions also include plants having an increased level/activity of the kn1 polypeptide of the invention wherein the plant maintains floral, pod and seed tissues or has an increase in the number of floral, pod and seed tissues.

V. Modulating the Stress Tolerance of a Plant

Methods are provided for the use of the kn1 sequences of the invention to modify the tolerance of a plant to abiotic stress. Increased growth of seedlings or early vigor is often associated with an increase in stress tolerance. For example, faster development of seedlings, including the root system of seedlings upon germination, is critical for survival, particularly under adverse conditions such as drought. Promoters that can be used in this method are described elsewhere herein, including low-level constitutive, inducible or root-preferred promoters, such as root-preferred promoters derived from ZmIPT4 and ZmIPT5 regulatory sequences. Accordingly, in one method of the invention, a plant's tolerance to stress is increased or maintained when compared to a control plant by increasing the level of kn1 activity in the germinating seedling. In other methods, a kn1 nucleotide sequence is provided by introducing into the plant a polynucleotide comprising a kn1 nucleotide sequence of the invention, expressing the kn1 sequence and thereby increasing the plant's tolerance to stress. In other embodiments, the kn1 nucleotide construct introduced into the plant is stably incorporated into the genome of the plant.

Methods are also provided to increase or maintain seed set during abiotic stress episodes. During periods of stress (i.e., drought, salt, heavy metals, temperature, etc.) embryo development is often aborted. In maize, halted embryo development results in aborted kernels on the ear (Cheikh and Jones, (1994) *Plant Physiol.* 106:45-51; Dietrich, et al., (1995) *Plant Physiol Biochem* 33:327-336). In soy, abortion of pods prior to seed maturation can reduce seed yield and is observed during both optimal and stress conditions. Preventing this seed loss will maintain yield. Accordingly, methods are provided to increase the stress resistance in a plant (e.g., during flowering and seed development). Increasing expression of the kn1 sequence of the invention can also modulate floral development during periods of stress and thus methods are provided to maintain or improve the flowering process in plants under stress. The method comprises increasing the level and/or activity of the kn1 sequence of the invention. In one method, a kn1 nucleotide sequence is introduced into the plant and the level and/or activity of the kn1 polypeptide is increased, thereby maintaining or improving the tolerance of the plant under stress conditions. In other methods, the kn1 nucleotide construct introduced into the plant is stably incorporated into the genome of the plant. See, for example, WO 00/63401.

Significant yield instability can occur as a result of unfavorable environments during the lag phase of seed development. During this period, seeds undergo dramatic changes in ultra structure, biochemistry and sensitivity to environmental perturbation, yet demonstrate little change in dry mass accumulation. Two important events that occur during the lag phase are initiation and division of endosperm cells and amyloplasts (which are the sites for starch deposition). It has been demonstrated that during the lag phase (around 10-12 days after pollination (DAP) in maize) a dramatic increase in cytokinin concentration immediately precedes maximum rates of endosperm cell division and amyloplast formation, indicating that this hormone plays a central role in these processes and in what is called the 'sink strength' of the developing seed. Cytokinins have been demonstrated to play an important role in establishing seed size, decreasing seed abortion and increasing seed set during unfavorable environmental conditions. For example, elevated temperatures affect seed formation. Elevated temperatures can inhibit the accumulation of cytokinin, decrease endosperm cell division and amyloplast number, and as a consequence, increase kernel abortion.

In crop species such as maize, kernel sink capacity is principally a function of the number of endosperm cells and starch granules established during the first 6 to 12 DAP. The final number of endosperm cells and amyloplasts formed is highly correlated with final kernel weight. (Capitanio, et al., (1983); Reddy and Daynard, (1983); Jones, et al., (1985) (1996); Engelen-Eigles, et al., (2000)). Hormones, especially cytokinins, have been shown to stimulate cell division, plastid initiation and other processes important in the establishment of kernel sink capacity (Davies, (1987)). Cytokinin levels could for example be manipulated in soybean using the GmIPT2 promoter to drive the expression of the kn1 gene. Similarly, endosperm- and/or pedicel-preferred promoters could be used to increase the level and/or duration of expression of kn1, which would result in an increase of cytokinin levels or other gene products that in turn increase flower and/or pod retention, increasing sink strength and yield. Methods are therefore provided to increase the activity and/or level of kn1 polypeptides in the developing inflorescence, thereby elevating cytokinin levels or other gene products and allowing developing seed to achieve their full genetic potential for size, minimize pod and/or seed abortion and buffer seed set during unfavorable environments. The methods further allow the plant to maintain and/or improve the flowering process during unfavorable environments.

In this embodiment, a variety of promoters could be used to direct the expression of a sequence capable of increasing the level and/or activity of the kn1 polypeptide, including but not limited to, seed-preferred promoters, developing-seed promoters, meristem-preferred promoters, stress-induced promoters and inflorescence-preferred (such as developing female inflorescence) promoters, seed-preferred promoters and pod-preferred promoters. In one method, a promoter that is stress insensitive and is expressed in a tissue of the developing seed during the lag phase of development is used. By "insensitive to stress" is intended that the expression level of a sequence operably linked to the promoter is not altered or is only minimally altered under stress conditions. By "lag phase" promoter is intended a promoter that is active in the lag phase of seed development as known in the art. By "developing-seed-preferred" is intended a promoter that allows for enhanced kn1 expression within a developing seed. Such promoters that are stress insensitive and are expressed in a tissue of the developing seed during the lag phase of development are known in the art and include Zag2.1 (Theissen, et al., (1995) Gene 156:155-166, GenBank Accession Number X80206) and mzE40 (Zm40) (U.S. Pat. No. 6,403,862 and WO 01/2178).

An expression construct may further comprise nucleotide sequences encoding peptide signal sequences in order to effect changes in cytokinin level or other gene products and/or activity in the mitochondria or chloroplasts. See, for example, Neupert, (1997) *Annual Rev. Biochem.* 66:863-917; Glaser, et al., (1998) *Plant Molecular Biology* 38:311-338; Duby, et al., (2001) *The Plant J* 27(6):539-549.

Methods to assay for an increase in seed set during abiotic stress are known in the art. For example, plants having the increased kn1 activity can be monitored under various stress conditions and compared to control plants. For instance, plants can be subjected to various degrees of stress during flowering and seed set. Under identical conditions, the genetically modified kn1 plant will have a higher number of developing pods and/or seeds than a control plant.

Accordingly, the present invention further provides plants having increased yield or a maintained yield and/or an increased or maintained flowering, seed or pod set or seed or pod retention during periods of abiotic stress (drought, salt, heavy metals, temperature extremes, etc.). In some embodiments, the plants having an increased or maintained yield during abiotic stress have an increased level/activity of the kn1 polypeptide of the invention. In some embodiments, the plant comprises a kn1 nucleotide sequence of the invention operably linked to a promoter that drives expression in the plant cell. In some embodiments, such plants have stably incorporated into their genome a nucleic acid molecule comprising a kn1 nucleotide sequence of the invention operably linked to a promoter that drives expression in the plant cell.

VI. Antibody Creation and Use

Antibodies can be raised to a protein of the present invention, including variants and fragments thereof, in both their naturally-occurring and recombinant forms. Many methods of making antibodies are known to persons of skill. A variety of analytic methods are available to generate a hydrophilicity profile of a protein of the present invention. Such methods can be used to guide the artisan in the selection of peptides of the present invention for use in the generation or selection of antibodies which are specifically reactive, under immunogenic conditions, to a protein of the present invention. See, e.g., Janin, (1979) *Nature,* 277:491-492; Wolfenden, et al., (1981) *Biochemistry* 208:49-855; Kyte and Doolittle, (1982) *J. Mol. Biol.* 157:105-132; Rose, et al., (1985) Science 229: 834-838. The antibodies can be used to screen expression libraries for particular expression products such as normal or abnormal protein or altered levels of the same, which may be useful for detecting or diagnosing various conditions related to the presence of the respective antigens. Assays indicating high levels of a KN1 protein of the invention, for example, could be useful in detecting plants, or specific plant parts, with elevated cytokinin levels. Usually the antibodies in such a procedure are labeled with a moiety which allows easy detection of presence of antigen/antibody binding.

The following discussion is presented as a general overview of the techniques available, however, one of skill will recognize that many variations upon the following methods are known.

A number of immunogens are used to produce antibodies specifically reactive with a protein of the present invention. Polypeptides encoded by isolated recombinant, synthetic or native polynucleotides of the present invention are the preferred antigens for the production of monoclonal or polyclonal antibodies. Polypeptides of the present invention are optionally denatured, and optionally reduced, prior to injection into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an antigen, preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Specific monoclonal and polyclonal antibodies will usually have an antibody binding site with an affinity constant for its cognate monovalent antigen at least between $10^6$-$10^7$, usually at least $10^8$, $10^9$, $10^{10}$ and up to about $10^{11}$ liters/mole. Further fractionation of the antisera to enrich for antibodies reactive to the protein is performed where desired (See, e.g., Coligan, (1991) *Current Protocols in Immunology*, Wiley/Greene, N.Y. and Harlow and Lane, (1989) *Antibodies: A Laboratory Manual*, Cold Spring Harbor Press, NY).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, often 15 to 20 amino acids in length and may be longer. The peptides are typically coupled to a carrier protein (e.g., as a fusion protein) or are recombinantly expressed in an immunization vector. Antigenic determinants on peptides to which antibodies bind are typically 3 to 10 amino acids in length.

Monoclonal antibodies are prepared from hybrid cells secreting the desired antibody. Monoclonal antibodies are screened for binding to a protein from which the antigen was derived. Description of techniques for preparing such monoclonal antibodies are found in, e.g., *Basic and Clinical Immunology*, 4th ed., Stites, et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986) and Kohler and Milstein, (1975) *Nature* 256:495-497. Summarized briefly, this method proceeds by injecting an animal with an antigen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secretes a single antibody species to the antigen. In this manner, the individual antibody species obtained are the products of immortalized and cloned single B cells generated by the animal in response to a specific site recognized on the antigenic substance.

Other suitable techniques involve selection of libraries of recombinant antibodies in phage or similar vectors (see, e.g., Huse, et al., (1989) *Science* 246:1275-1281 and Ward, et al., (1989) *Nature* 341:544-546 and Vaughan, et al., (1996) *Nature Biotechnology*, 14:309-314). Also, recombinant immunoglobulins may be produced. See, Cabilly, U.S. Pat. No. 4,816,567 and Queen, et al. (1989), *Proc. Nat'l Acad. Sci.* 86:10029-10033.

Antibodies to the polypeptides of the invention are also used for affinity chromatography in isolating proteins of the present invention. Columns are prepared, e.g., with the antibodies linked to a solid support, e.g., particles, such as agarose, SEPHADEX®, or the like, where a cell lysate is passed through the column, washed and treated with increasing concentrations of a mild denaturant, whereby purified proteins are released.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

VII. Protein Immunoassays

Means of detecting the proteins of the present invention are not critical aspects of the present invention. In certain examples, the proteins are detected and/or quantified using any of a number of well-recognized immunological binding assays (see, e.g., U.S. Pat. Nos. 4,366,241; 4,376,110; 4,517, 288 and 4,837,168). For a general review of immunoassays, see also, Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B. V., Amsterdam (1985); Harlow and Lane, supra; *Immunoassay: A Practical Guide*, Chan, Ed., Academic Press, Orlando, Fla. (1987); *Principles and Practice of Immunoassaysm*, Price and Newman Eds., Stockton Press, NY (1991); and *Non-isotopic Immunoassays*, Ngo, Ed., Plenum Press, NY (1988).

Immunological binding assays (or immunoassays) typically utilize a "capture agent" to specifically bind to and often immobilize the analyte (in this case, a protein of the present invention). The capture agent is a moiety that specifically binds to the analyte. In certain embodiments, the capture agent is an antibody that specifically binds a protein of the present invention. The antibody may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled protein of the present invention or a labeled antibody specifically reactive to a protein of the present invention. Alternatively, the labeling agent may be a third moiety, such as another antibody, that specifically binds to the antibody/protein complex.

Throughout the assays, incubation and/or washing steps may be required after each combination of reagents. Incubation steps can vary from about 5 seconds to several hours, often from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting a protein of the present invention in a biological sample generally comprises the steps of contacting the biological sample with an antibody which specifically reacts, under immunologically reactive conditions, to a protein of the present invention. The antibody is allowed to bind to the protein under immunologically reactive conditions and the presence of the bound antibody is detected directly or indirectly.

A. Non-Competitive Assay Formats

Immunoassays for detecting proteins of the present invention include competitive and noncompetitive formats. Non-competitive immunoassays are assays in which the amount of captured analyte (i.e., a protein of the present invention) is directly measured. In one example, the "sandwich" assay, the capture agent (e.g., an antibody specifically reactive, under immunoreactive conditions, to a protein of the present invention) can be bound directly to a solid substrate where it is immobilized. These immobilized antibodies then capture the protein present in the test sample. The protein thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

B. Competitive Assay Formats

In competitive assays, the amount of analyte present in the sample is measured indirectly by measuring the amount of an added (exogenous) analyte (e.g., a protein of the present invention) displaced (or competed away) from a capture agent (e.g., an antibody specifically reactive, under immunoreactive conditions, to the protein) by the analyte present in the sample. In one competitive assay, a known amount of analyte is added to the sample and the sample is then contacted with a capture agent that specifically binds a protein of the present invention. The amount of protein bound to the capture agent is inversely proportional to the concentration of analyte present in the sample.

In one embodiment, the antibody is immobilized on a solid substrate. The amount of protein bound to the antibody may be determined either by measuring the amount of protein present in a protein/antibody complex or alternatively by measuring the amount of remaining uncomplexed protein. The amount of protein may be detected by providing a labeled protein.

A hapten inhibition assay is another competitive assay. In this assay a known analyte, such as a protein of the present invention, is immobilized on a solid substrate. A known amount of antibody specifically reactive, under immunoreactive conditions, to the protein is added to the sample, and the sample is then contacted with the immobilized protein. In this case, the amount of antibody bound to the immobilized protein is inversely proportional to the amount of protein present in the sample. Again, the amount of immobilized antibody may be determined by detecting either the immobilized fraction of antibody or the fraction of the antibody that remains in solution. Detection may be direct, where the antibody is labeled, or indirect, by the subsequent addition of a labeled moiety that specifically binds to the antibody, as described above.

C. Generation of Pooled Antisera for use in Immunoassays

A protein that specifically binds to, or that is specifically immunoreactive with, an antibody generated against a defined antigen is determined in an immunoassay. The immunoassay uses a polyclonal antiserum which is raised to a polypeptide of the present invention (i.e., the antigenic polypeptide). This antiserum is selected to have low cross-reactivity against other proteins, and any such cross-reactivity is removed by immunoabsorbtion prior to use in the immunoassay (e.g., by immunosorbtion of the antisera with a protein of different substrate specificity (e.g., a different enzyme) and/or a protein with the same substrate specificity but of a different form).

In order to produce antisera for use in an immunoassay, a polypeptide of the present invention is isolated as described herein. For example, recombinant protein can be produced in a mammalian or other eukaryotic cell line. An inbred strain of mice is immunized with the protein using a standard adjuvant, such as Freund's adjuvant, and a standard mouse immunization protocol (see, Harlow and Lane, supra). Alternatively, a synthetic polypeptide derived from the sequences disclosed herein and conjugated to a carrier protein is used as an immunogen. Polyclonal sera are collected and tittered against the immunogenic polypeptide in an immunoassay, for example, a solid phase immunoassay with the immunogen immobilized on a solid support. Polyclonal antisera with a titer of $10^4$ or greater are selected and tested for their cross reactivity against polypeptides of different forms or substrate specificity, using a competitive binding immunoassay such as the one described in Harlow and Lane, supra, at pages 570-573. Preferably, two or more distinct forms of polypeptides are used in this determination. These distinct types of polypeptides are used as competitors to identify antibodies which are specifically bound by the polypeptide being assayed for. The competitive polypeptides can be produced as recombinant proteins and isolated using standard molecular biology and protein chemistry techniques as described herein.

Immunoassays in the competitive binding format are used for cross-reactivity determinations. For example, the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent cross-reactivity for the above proteins is calculated, using standard methods. Those antisera with less than 10% cross-reactivity for a distinct form of a polypeptide are selected and pooled. The cross-reacting antibodies are then removed from the pooled antisera by immunoabsorbtion with a distinct form of a polypeptide.

The immunoabsorbed and pooled antisera are then used in a competitive binding immunoassay as described herein to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

D. Other Assay Formats

In certain embodiments, Western blot (immunoblot) analysis is used to detect and quantify the presence of protein of the present invention in the sample. The technique generally comprises separating sample proteins by gel electrophoresis on the basis of molecular weight, transferring the separated proteins to a suitable solid support (such as a nitrocellulose filter, a nylon filter or derivatized nylon filter) and incubating the sample with the antibodies that specifically bind a protein of the present invention. The antibodies specifically bind to the protein on the solid support. These antibodies may be directly labeled, or may be subsequently detected using labeled antibodies (e.g., labeled sheep anti-mouse antibodies) that specifically bind to the antibodies.

E. Quantification of Proteins.

The proteins of the present invention may be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays and the like.

F. Reduction of Non-Specific Binding

One of skill will appreciate that it is often desirable to reduce non-specific binding in immunoassays and during analyte purification. Where the assay involves an antigen, antibody or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk and gelatin are widely used.

G. Immunoassay Labels

The labeling agent can be, e.g., a monoclonal antibody, a polyclonal antibody, a binding protein or complex or a polymer such as an affinity matrix, carbohydrate or lipid. Detectable labels suitable for use in the present invention include any composition detectable by spectroscopic, radioisotopic, photochemical, biochemical, immunochemical, electrical, optical or chemical means. Detection may proceed by any known method, such as immunoblotting, Western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis or other methods which track a molecule based upon an alteration in size and/or charge. The particular label or detectable group used in the assay is not a critical aspect of the invention. The detectable group can be any material having a detectable physical or chemical property, including magnetic beads, fluorescent dyes, radiolabels, enzymes and colorimetric labels or colored glass or plastic beads, as discussed for nucleic acid labels, supra. The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation and disposal provisions. Means of detecting labels are well known to those of skill in the art.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound or a chemiluminescent compound. A number of ligands and anti-ligands can be used.

The molecules can also be conjugated directly to signal-generating compounds, e.g., by conjugation with an enzyme or fluorophore. Enzymes of interest as labels will primarily be hydrolases, particularly phosphatases, esterases and glycosidases or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal-producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Compounds that Modulate Enzymatic Activity or Expression

A catalytically active polypeptide of the present invention may be contacted with a compound in order to determine whether said compound binds to and/or modulates the enzymatic activity of such polypeptide. The polypeptide employed will have at least 20%, 30%, 40%, 50%, 60%, 70% or 80% of the specific activity of the native, full-length enzyme of the present invention. Generally, the polypeptide will be present in a range sufficient to determine the effect of the compound, typically about 1 nM to 10 μM. Likewise, the compound being tested will be present in a concentration of from about 1 nM to 10 μM. Those of skill will understand that such factors as enzyme concentration, ligand concentrations (i.e., substrates, products, inhibitors, activators), pH, ionic strength and temperature will be controlled so as to obtain useful kinetic data and determine the presence or absence of a compound that binds or modulates polypeptide activity. Methods of measuring enzyme kinetics are well known in the art. See, e.g., Segel, (1976) *Biochemical Calculations*, 2$^{nd}$ ed., John Wiley and Sons, New York.

The following examples are offered by way of illustration and not by way of limitation.

EXAMPLES

Example 1

Soy Transgenic for Maize Knotted1 (ZmKn1) Shows Increased Yield

The maize knotted1 (kn1) gene encodes a nuclear homeobox (homeodomain) protein, which is thought to be a transcription factor important for maintaining the meristematic state of cells, thus being involved in regulation of cell development and differentiation (Vollbrecht, et al., 1991). It is a member of a family of closely related homeobox genes in maize. Zm-kn1 homologues have been isolated from rice, *Arabidopsis*, soybean, tomato and tobacco (see, references cited herein). Dominant mutations affecting the level, timing, or location of expression of this protein can result in gross morphological changes (Smith, et al., 1992).

The soybean annexin promoter (Gm-ann PRO) drives expression of Zm-kn1 in PHP24677A. The promoter is described in U.S. Pat. No. 7,129,089, EP1592799A2 and WO 2004/071178A2. The annexin promoter is an embryo- and seed-preferred promoter in soybean; it is most active in developing seeds at early stages (within 10 days after pollination) and is largely quiescent in later stages. "PinII term" is a terminator from the proteinase inhibitor II gene of potato (*Solanum tuberosum*), a dicotyledonous plant of the Solanaceae family.

In divergent orientation to Gm-ann:Zmkn1:PinII term is the selectable marker gene SAMS:hra. "SAMS" indicates a promoter of the S-adenosyl-L-methionine synthetase gene (sams) from soybean (Falco and Li, (2007) U.S. Pat. No. 7,217,858). The GM-SAMS 5' UTR and GM-SAMS 5UTR2 are 5' untranslated regions of the sams gene from soybean and the GM-SAMS intron1 is an intron within the 5' untranslated region of the sams gene from soybean (Falco and Li, 2007). The GM-HRA is a modified version of the acetolactate synthase gene from soybean with 15 additional nucleotides on the 5' end, derived from the 5' untranslated region of the gm-als gene and two nucleotide changes within the coding sequence. The GM-ALS (HRA) TERM is a native terminator from the soybean acetolactate synthase gene.

Figure 1:
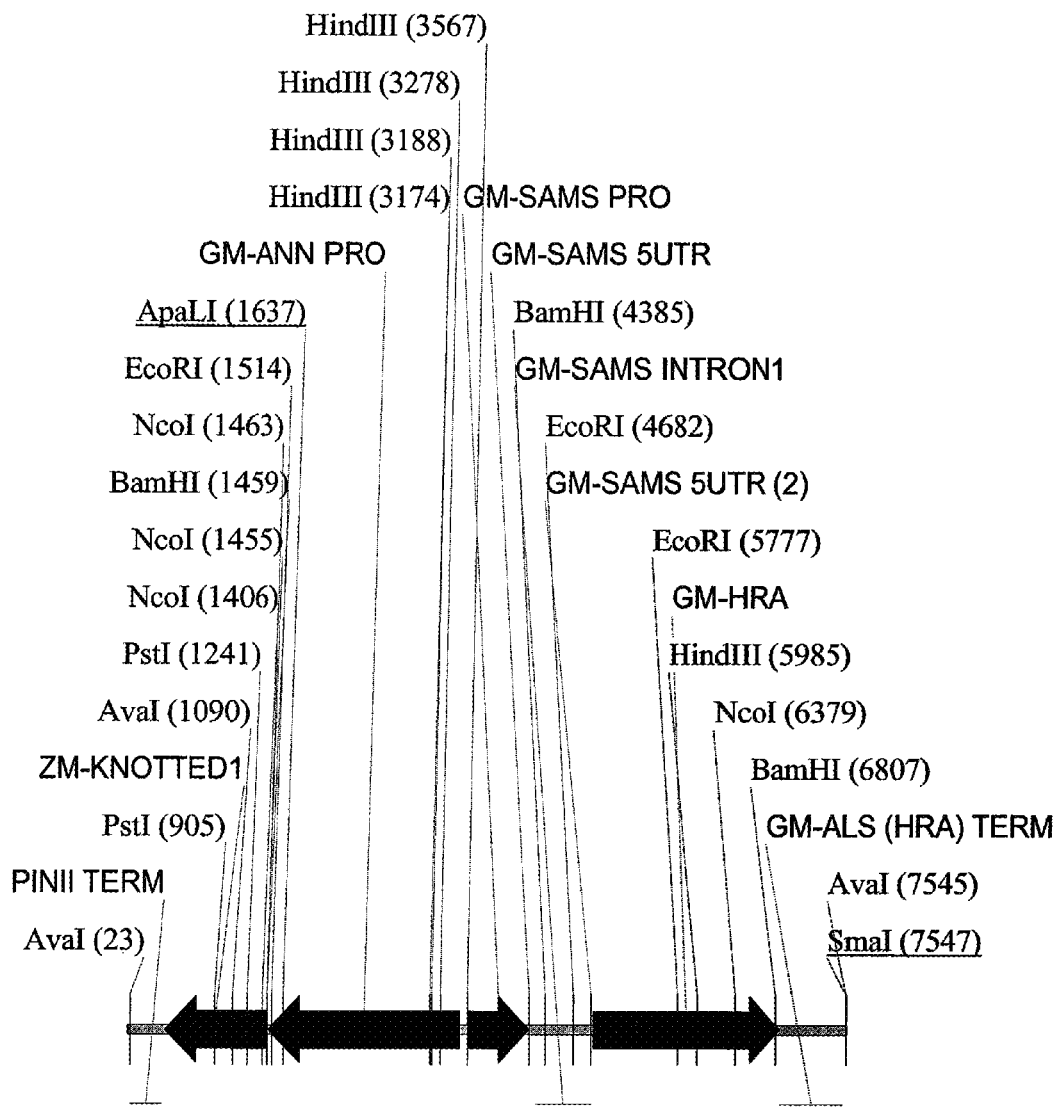
FIG. 1 is a linear map of PHP24677A.

Biolistic transformation of soybean with the linear DNA fragment PHP24677A containing the Gm-annexin:Zm-kn1:: SAMS:hra gene cassette leads to a novel phenotype characterized by increased yield and tolerance to ALS-inhibiting herbicides. A map of the construct is shown in FIG. 1. The sequence is provided in SEQ ID NO: 1. FIG. 2 describes the position and orientation of the various components of the construct.

Near-isogenic lines (isolines) of Gm-ann:Zm-kn1 events were created by selfing the T0 and T1 generation and identifying T2 plants that were either homozygous positive for presence of kn1 or homozygous negative (lacking the kn1 transgene). Zygosity of each T2 plant was determined by using quantitative PCR (qPCR) to determine copy number of the kn1 transgene. Seed of selected T2 plants was increased as single plant-to-row in the T3 generation to generate seed for preliminary yield testing in year 1. Seed of each isoline from the T4 and T5 generation was increased for advanced level yield testing in year 2 and 3, respectively. Isolines that were either homozygous kn1 positive or homozygous kn1 negative were tested in a randomized complete block yield test design, blocked by transgenic event. Yield testing plots consisted of paired 3.7 m rows with 76.2 cm row spacing. In year 1, the yield testing trials were grown in one replication at Cedar Falls, Iowa, Johnston, Iowa and Stuart, Iowa. In year 2, the yield trials were grown in single replication at Princeton, Ill. and Napoleon, Ohio and in three replications at Johnston, Iowa, Stuart, Iowa and Champaign, Ill. In year 3, the yield trials were grown in two replications at Princeton, Ill., Champaign, Ill. and Napoleon, Ohio and in three replications at Johnston, Iowa, Stuart, Iowa and Washington, Iowa. Statistical analyses for yield and maturity data were completed using the mixed model of SAS® (SAS Institute, Inc., Cary, N.C., USA).

When yield data for all events were examined by year, all positive isolines had a significantly higher yield average compared to all negative isolines in year 1 (+1.2 bu/ac; +3.2%) and year 3 (+0.7 bu/ac; +1.9%) (Table 1A). Data from year 2 were not significant; however, when all yield data were combined from year 1 through year 3, all positive isolines had a significantly higher yield average compared to all negative isolines (+0.8 bu/ac; +2.0%) (Table 1A).

When yield data were examined on an event basis, EAFS 4265.6.8 had kn1 positive isolines with a significantly higher yield average compared to negative sister isolines in year 1. In year 1, EAFS 4271.2.1 had kn1 negative isolines with a significantly higher yield average compared to kn1 positive sister isolines. In year 2, there were nine events where kn1 positive isolines had a significantly higher yield advantage compared to kn1 negative sister isolines, ranging from +2.4 bu/ac (+4.8%) to +5.5 bu/a (+12.3%). Three events had kn1 negative isolines with a significantly higher yield average compared to kn1 positive isolines in year 2. For year 3, kn1 positive isolines of seven events had a significantly higher yield average compared to their respective kn1 negative sister isolines, ranging from +0.7 bu/ac (+1.9%) to +5.2 bu/ac (+15.2%). Two events had kn1 negative isolines with a significant yield advantage compared to kn1 positive sister lines in year 3. Combining all data for all three years, there were nine events with kn1 positive isolines significantly outyielding the transgene-negative isolines, with the difference ranging from +1.7 bu/ac (+4.0%) to +4.2 bu/ac (+10.8%) (Table 1B). EAFS 4265.7.3 and EAFS 4271.2.1 had kn1 negative isolines with a yield advantage compared to kn1 positive sister lines (Table 1 B). This may be related to aberrant kn1 expression, as constitutive expression of kn1 was observed to be detrimental to overall yield in soybean (data not shown).

Table 1A provides the difference of yield least squares mean (LSMean) estimates for all positive kn1 isolines compared to all negative kn1 isolines from 15 events of PHP24677A, tested over three years.

TABLE 1A

| YEAR | Total Reps | EVENT | kn1 POS LSMean | Kn1 neg LSMean | % Increase | Yield Difference | Difference Prob < t |
|---|---|---|---|---|---|---|---|
| 1 | 3 | ALL | 37.7 | 36.6 | 3.2 | 1.2 | 0.022 |
| 2 | 11 | ALL | 47.8 | 47.3 | 1.1 | 0.5 | 0.223 |
| 3 | 15 | ALL | 39.0 | 38.2 | 1.9 | 0.7 | 0.049 |
| 1 + 2 + 3 | 29 | ALL | 41.5 | 40.7 | 2.0 | 0.8 | 0.002 |

Table 1B shows the difference of yield least squares mean estimates for kn1 positive isolines compared to sister kn1 negative isolines from 15 events of PHP24677A, tested over 3 years at 7 geographic locations with a total of 29 replications.

TABLE 1B

| Event | Difference[1] vs. construct-null | Probability | % Increase |
|---|---|---|---|
| EAFS 4267.1.1 | 4.2 | 0 | 10.8 |
| EAFS 4271.4.4 | 3.7 | 0 | 9.7 |

TABLE 1B-continued

| Event | Difference[1] vs. construct-null | Probability | % Increase |
|---|---|---|---|
| EAFS 4265.6.8 | 3.3 | 0 | 8.7 |
| EAFS 4267.1.4 | 3.0 | 0 | 7.8 |
| EAFS 4271.2.6 | 2.7 | 0.001 | 6.5 |
| EAFS 4267.4.6 | 2.7 | 0.017 | 6.6 |
| EAFS 4271.5.1 | 2.1 | 0.012 | 4.9 |
| EAFS 4267.1.3 | 1.9 | 0.069 | 4.7 |
| EAFS 4267.4.3 | 1.7 | 0.051 | 4.0 |
| EAFS 4271.3.1 | 1.4 | 0.217 | 3.3 |
| EAFS 4271.3.2 | 0.9 | 0.337 | 2.3 |
| EAFS 4271.2.5 | 0.7 | 0.418 | 1.6 |
| EAFS 4271.4.1 | 0.5 | 0.562 | 1.1 |
| EAFS 4265.7.3 | −5.8 | 0 | −14.8 |
| EAFS 4271.2.1 | −10.6 | 0 | −23.9 |

[1]Bushels per acre

Figure 6:
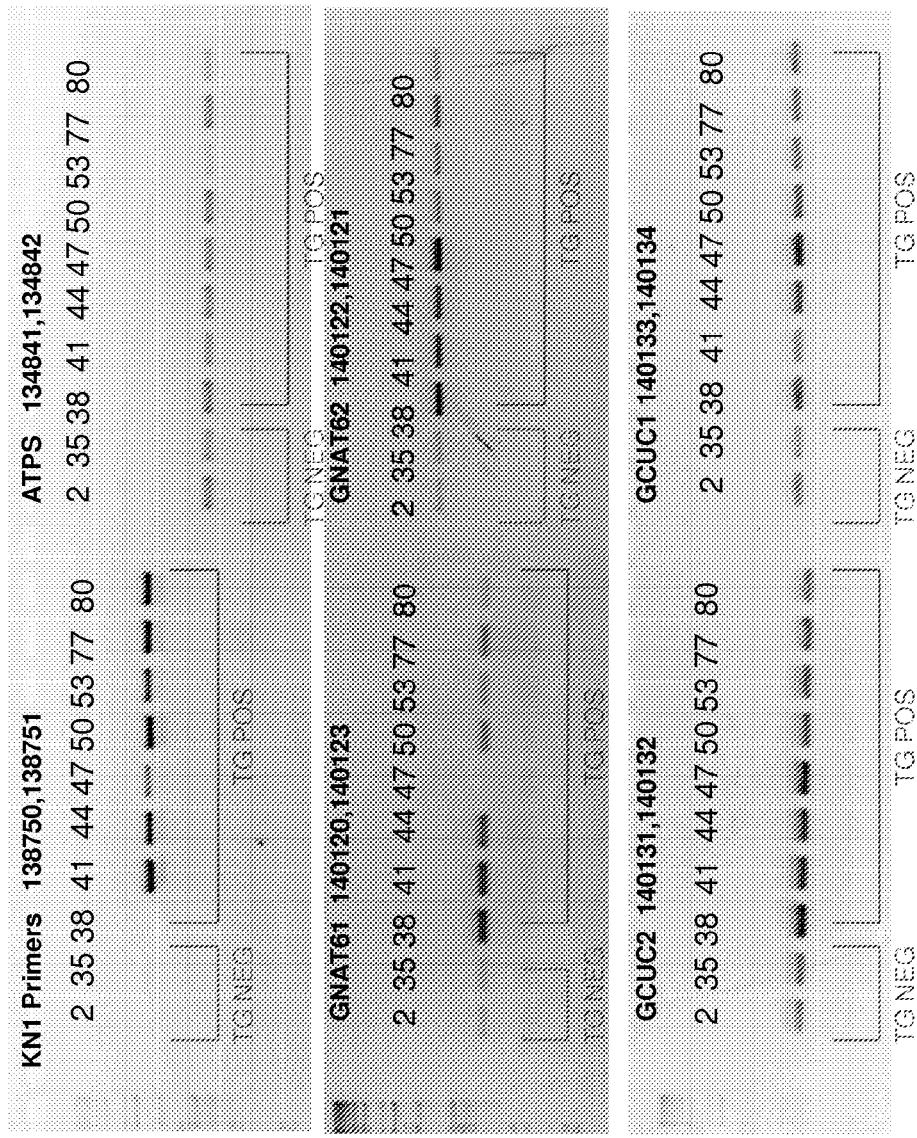
FIG. 6 shows upregulation of kn1 target genes in ann:kn1 transgenics.

The kn1 events were further analyzed for expression of the transgene. Using standard mass spectrometry methods, peaks representing kn1 amino acid signatures (FIG. 4) were detected in the transgene-positive plant tissues; corresponding peaks were not detected in control tissues. Second, transgene positive seeds (less than 5 mm in size) were analyzed for cytokinin content. Several events showed significantly increased levels of two abundant cytokinins, zeatin riboside and dihydroxyzeatin riboside. (FIG. 5) Tissues sampled were seeds of <5 mm from plants grown in the field (A) or in growth chamber (B). Error bars represent the 95% confidence level. Third, RT-PCR was used to assess expression of genes previously identified as KN1 targets (Liu, et al., (2008) *J. Genet. Genom.* 35:441-449). As expected, expression of these target genes was upregulated in the transgene-positive events. See, FIG. 6. ATPS is control; Gnat61, Gnat62, Gcuc2, Gcuc1 are soybean genes related to the shoot apical meristem function.

Example 2

Additional Constructs for Targeted Kn1 Expression

Figure 7:
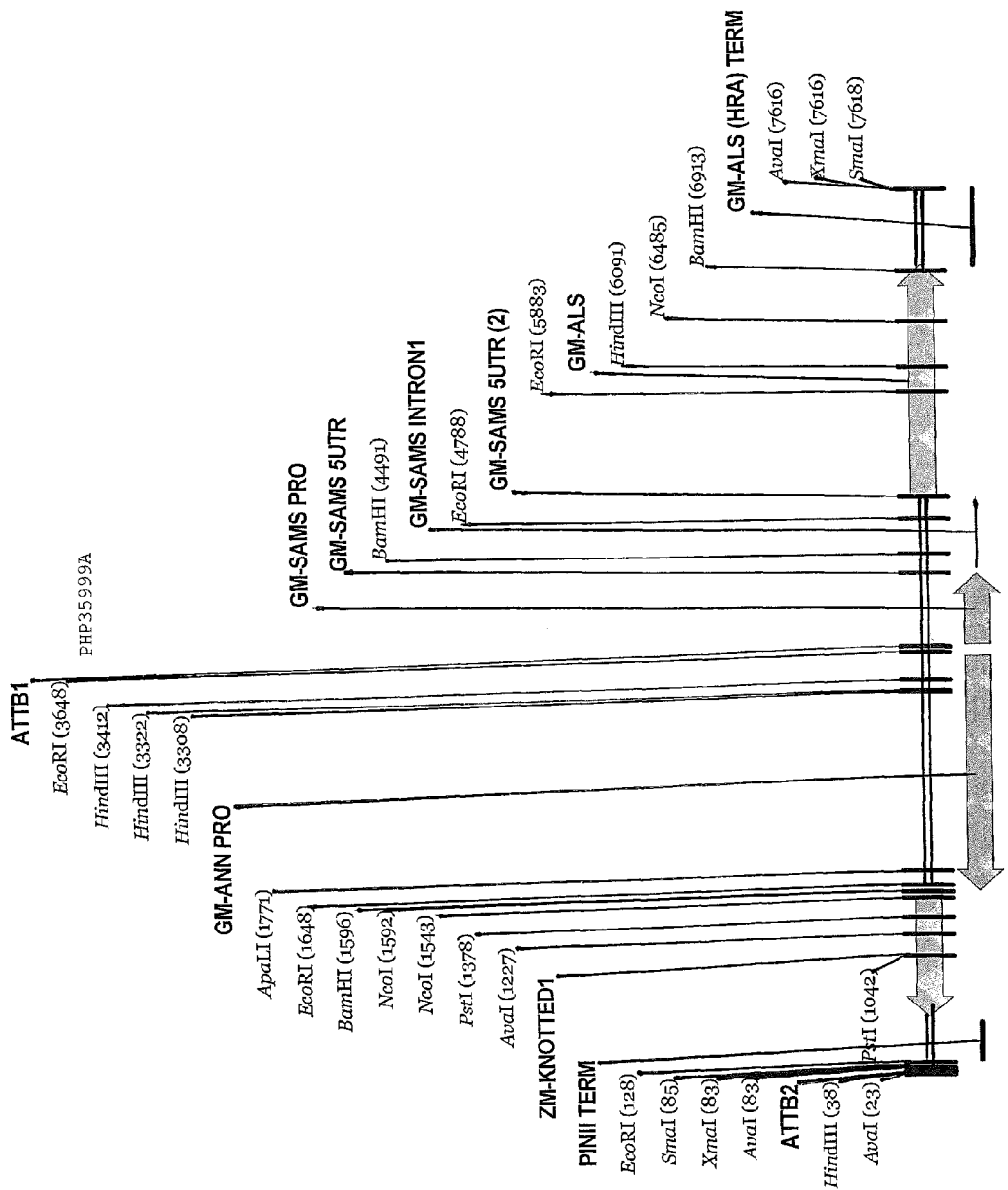
FIG. 7 is a linear map of PHP35999A.

Another embodiment is illustrated by SEQ ID NO: 2 and FIG. 7. As can be seen, this construct, PHP35999A, also comprises the soy annexin promoter operably linked to maize kn1. However, it lacks the overlapping open reading frame of PHP24677A. Further embodiments may substitute, in place of the annexin promoter, other promoters which drive expression preferentially in developing floral or seed tissues, such as the *Arabidopsis* Lec2 promoter, the soy Ltp2 promoter and other tissue-preferred promoters such as those listed elsewhere herein. Further, the construct may comprise a kn1 gene from another species, such as *Arabidopsis*, wheat, sorghum or rice.

Example 3

Soybean Embryo Transformation

Soybean embryos are bombarded with a plasmid containing the Maize ZM-knotted1, driven by GM-annexin promoter as follows. To induce somatic embryos, cotyledons, 3-5 mm in length dissected from surface-sterilized, immature seeds of the soybean cultivar Jack, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) *Nature* (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The expression cassette comprising the ZM knotted1 sequence operably linked to the GM annexin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 4

Sunflower Meristem Tissue Transformation

Sunflower meristem tissues are transformed with an expression cassette containing ZM-knotted1, driven by GM-annexin promoter, as follows (see also, EP Patent Number EP 0 486233, herein incorporated by reference and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% Clorox® bleach solution with the addition of two drops of Tween® 20™ surfactant per 50 ml of solution. The seeds are rinsed twice with sterile distilled water.

Split embryonic axis explants are prepared by a modification of procedures described by Schrammeijer, et al. (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.* 15:473-497), Shepard's vitamin additions (Shepard, (1980) in *Emergent Techniques for the Genetic Improvement of Crops* (University of Minnesota Press, St. Paul, Minn.)), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6 and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS1000® particle acceleration device.

Disarmed *Agrobacterium tumefaciens* strain EHA105 is used in all transformation experiments. A binary plasmid vector comprising the expression cassette that contains the Maize ZM-knotted1, driven by GM-annexin promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bacto® peptone and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$ and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for cytokinin synthesis activity. Such assays are described elsewhere herein.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% Gelrite® gelling agent, pH 5.6) and grown under conditions described for explant culture. The upper portion of the seedling is removed, a 1 cm vertical slice is made in the hypocotyl, and the transformed shoot inserted into the cut. The entire area is wrapped with Parafilm® tape to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by cytokinin synthesis activity analysis of leaf extracts while transgenic seeds harvested from NPTII-positive $T_0$ plants are identified by cytokinin synthesis activity analysis of small portions of dry seed cotyledon. Example 5

Variants of Knotted1

A. Variant Nucleotide Sequences of Knotted 1 That Do Not Alter the Encoded Amino Acid Sequence The knotted1 nucleotide sequences set forth in herein and in references described herein are used to generate variant nucleotide sequences having the nucleotide sequence of the open reading frame with about 70%, 75%, 80%, 85%, 90% or 95% nucleotide sequence identity when compared to the corresponding starting unaltered ORF nucleotide sequence. These functional variants are generated using a standard codon table. While the nucleotide sequence of the variant is altered, the amino acid sequence encoded by the open reading frame does not change.

B. Variant Amino Acid Sequences of knotted 1

Variant amino acid sequences of knotted1 are generated. In this example, one or more amino acids are altered. Specifically, the open reading frame set forth in FIG. 3 is reviewed to determine the appropriate amino acid alteration. The selection of an amino acid to change is made by consulting a protein alignment with orthologs and other gene family members from various species. An amino acid is selected that is deemed not to be under high selection pressure (not highly conserved) and which is rather easily substituted by an amino acid with similar chemical characteristics (i.e., similar functional side-chain). Assays as outlined elsewhere herein may be followed to confirm functionality. Variants having about 70%, 75%, 80%, 85%, 90% or 95% nucleic acid sequence identity to sequences disclosed and incorporated herein are generated using this method.

C. Additional Variant Amino Acid Sequences of knotted 1

In this example, artificial protein sequences are created having 80%, 85%, 90% and 95% or more identity relative to the reference protein sequence. This latter effort requires identifying conserved and variable regions from the alignments generated using methods and procedures known in the art, such as BLAST alignments and then the judicious application of an amino acid substitutions table. These parts will be discussed in more detail below.

Largely, the determination of which amino acid sequences are altered is made based on the conserved regions among the KNOTTED1 proteins or among the other knotted 1 transcription factor polypeptides. Based on the sequence alignment, the various regions of the knotted polypeptides that can likely be altered can be determined. It is recognized that conservative substitutions can be made in the conserved regions without altering function. In addition, one of skill will understand that functional variants of the ZM knotted1 of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided, supra.

First, any conserved amino acids in the protein that should not be changed are identified and "marked off" for insulation from the substitution. The start methionine will of course be added to this list automatically. Next, the changes are made. H, C and P are not changed. The changes will occur with isoleucine first, sweeping N-terminal to C-terminal. Then leucine, and so on down the list until the desired target is reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of ZM knotted1-1 and ZM knotted1-2 are generated having about 82%, 87%, 92%, and 97% amino acid identity to the starting unaltered ORF nucleotide sequence herein.

TABLE 2

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |

TABLE 2-continued

Substitution Table

| Amino Acid | Strongly Similar and Optimal Substitution | Rank of Order to Change | Comment |
|---|---|---|---|
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

Example 6

Amplification of Additional Knotted1 Genes from Other Plant Species

Additional knotted1 genes from plant species could be identified by PCR or RT-PCR methods using degenerate primers such as the ones described below. Degenerate primers can be designed against conserved amino acid motifs found in available KNOTTED1 proteins, such as those from soybean, maize, rice or *Arabidopsis*. Such motifs can be identified from an alignment of the protein sequences. Sense/antisense primers could be used in different combinations. Similarly, several rounds of PCR could be used. The product of amplification of one pair of sense/antisense primers could be used as template for PCR with another set of internal (nested) degenerate primers therefore maximizing the chances for amplification of an appropriate sequence, i.e., containing a sequence corresponding to the corresponding amino acid motif.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A transgenic plant comprising an isolated polynucleotide operably linked to a tissue-preferred promoter that drives expression preferentially in developing flower, pod, ear or seed tissue, wherein said polynucleotide encodes a knotted1 transcription factor and is 95% identical to the reverse complement of positions 378 through 1457 of SEQ ID NO:1, wherein yield is increased relative to a control plant.

2. The plant of claim 1, wherein flower, pod, ear and/or seed retention is increased.

3. The plant of claim 1, wherein the knotted1 transcription factor is native to *Zea mays*.

4. The plant of claim 1, wherein said promoter is annexin promoter native to *Glycine max*.

5. The plant of claim 1, wherein said operable linkage is as shown in FIG. 1.

6. The plant of claim 1, wherein said promoter is stress-insensitive and is expressed in a tissue of the developing seed or related maternal tissue at or about the time of anthesis.

7. A transformed seed of the plant of claim 1, wherein the seed comprises said polynucleotide.

8. The plant of claim 1, wherein said plant is maize, wheat, rice, barley, sorghum, rye, soybean, brassica or sunflower.

9. A method of increasing seed yield of a plant, comprising transforming a plant with an isolated polynucleotide, wherein said polynucleotide encodes a knotted1 transcription factor protein and is 95% identical to the reverse complement of positions 378 through 1457 of SEQ ID NO:1, said polynucleotide operably linked to tissue-preferred regulatory sequences directing expression preferentially in developing flowers, developing pods or ears or developing seeds.

10. The method of claim 9 wherein cytokinin level is increased.

11. The method of claim 9 wherein at least one of said operably-linked regulatory sequences is inducible.

12. The method of claim 9 wherein said regulatory sequences comprise a promoter that is stress-insensitive.

13. The method of claim 9 wherein said regulatory sequences comprise the *annexin* promoter native to *Glycine max*.

14. The method of claim 9 wherein knotted1 transcription factor level or activity is increased in one or more of the embryo, the endosperm, the cotyledon and tissues proximal thereto.

15. The method of claim 9, wherein said plant is maize, wheat, rice, barley, sorghum, rye, soybean, brassica or sunflower.

16. The method of claim 15 wherein said plant is soybean.

17. The method of claim 9 wherein said knotted1 gene is native to *Zea mays*.

18. A plant with increased seed yield produced by the method of claim 9.

* * * * *